United States Patent
Guo et al.

[11] Patent Number: 6,117,880
[45] Date of Patent: Sep. 12, 2000

[54] SOMATOSTATIN AGONISTS

[75] Inventors: Liangquin Guo, Edison; Ralph T. Mosley, Roselle; Alexander Pasternak, Princeton; Arthur A. Patchett, Westfield; Lihu Yang, Edison, all of N.J.

[73] Assignee: Merck & Co., Inc., Rahway, N.J.

[21] Appl. No.: 09/181,590

[22] Filed: Oct. 28, 1998

Related U.S. Application Data

[60] Provisional application No. 60/064,422, Oct. 30, 1997.

[51] Int. Cl.⁷ ........................ A61K 31/438; C07D 221/20

[52] U.S. Cl. ......................... 514/278; 546/16; 546/17; 546/18

[58] Field of Search .................. 546/16, 17, 18; 514/278

[56] References Cited

U.S. PATENT DOCUMENTS

| | | | |
|---|---|---|---|
| 4,242,347 | 12/1980 | Huebner | 514/324 |
| 4,310,518 | 1/1982 | Freidinger et al. | 514/11 |
| 5,360,807 | 11/1994 | Janssens et al. | 514/318 |
| 5,536,716 | 7/1996 | Chen | 514/215 |
| 5,710,155 | 1/1998 | Schnorrenberg | 514/255 |
| 5,767,118 | 6/1998 | Nargund | 514/226.4 |
| 5,869,489 | 2/1999 | Shah | 514/253 |

FOREIGN PATENT DOCUMENTS 2 311 523  10/1997  United Kingdom.

OTHER PUBLICATIONS

Rosenthal et al. "Structure activity relationship of somatostatin analogs . . . " CA 98:191905, 1983.

Betoin et al. "In vitro and in vivo evidence . . . " CA 123:26282, 1995.

Cavanak, T., et al., Chem. Abs., vol. 119, No. 23, Abs. No. 241372d, p. 69, 1993.

Maccoss, M., et al., Chem. Abs., vol. 128, No. 2, p. 386, Col. 1, Abs. No. 13436h, 1998.

Rudolf, K., et al., Chem. Abs., vol. 128, No. 19, p. 604, Abs. No. 230701v, 1998.

Yang, L., et al., Proc. Natl. Acad. Sci., vol. 95, No. 18, pp. 10836–10841, 1998.

Yang, L., et al., J. Med. Chem., vol. 41, No. 13, pp. 2175–2179, 1998.

*Primary Examiner*—Ceila Chang
*Attorney, Agent, or Firm*—James L. McGinnis; David L. Rose

[57] ABSTRACT

This invention relates to somatostatin agonist compounds which are potent with high selectivity toward the receptor subtype 2. The compounds provide an improved therapeutic index in the treatment of diabetes, cancer, acromegaly and retenosis. Many of the compounds are also orally active. Thus, it is an object of this invention to describe such compounds. It is a further object to describe the specific preferred stereoisomers of the somatostastin agonists. A still further object is to describe processes for the preparation of such compounds. Another object is to describe methods and compositions which use the compounds as the active ingredient thereof. Further objects will become apparent from reading the following description.

14 Claims, No Drawings

SOMATOSTATIN AGONISTS

CROSS REFERENCE TO RELATED APPLICATIONS

This application is a non-provisional application related to U.S. application Ser. No. 60/064,422, filed on Oct. 30, 1997 priority of which is claimed hereunder.

BACKGROUND OF THE INVENTION

Somatostatin (SST) is a widely distributed peptide occurring in two forms SST-14 (with 14 amino acids) and SST-28 (with 28 amino acids). SST has multiple functions including modulation of secretion of growth hormone, insulin, glucagon, pancreatic enzymes and gastric acid, in addition to having potent anti-proliferative effects.

The mechanism of action of somatostatin is mediated via high affinity membrane associated receptors. Five somatostatin receptors (SSTR1-5) are known (Reisine, T.; Bell, G. I. *Endocrine Reviews* 1995, 16, 427–442). All five receptors are heterogeneously distributed and pharmacologically distinct. Structure-function studies with a large number of peptidal analogs have shown that the Trp-Lys dipeptide of somatostatin is important for high-affinity binding. The availability of these receptors now makes it possible to design selectively active ligands for the sub-types to determine their physiological functions and to guide potential clinical applications. For example, studies utilizing subtype selective peptides have provided evidence that somatostatin subtype 2 receptors (SSTR2) mediates the inhibition of growth hormone release from the anterior pituitary and glucagon release from the pancreas, whereas SSTR5 selective agonists inhibit insulin release. These results imply the usefulness of SSTR2 selective analogs in the treatment of diabetes and many of the compounds of this invention have that selectivity.

In addition, the novel compounds described herein are useful in the therapy of a variety of conditions which include acromegaly, retinal neovascularization, neuropathic and visceral pain, irritable bowel syndrome, chronic atrophic gastritis, Crohn's disease, rheumatoid arthritis and sarcoidosis. The instant compounds inhibit cell proliferation and cause the regression of certain tumors including breast cancer and they are useful in preventing restenosis after angioplasty and to inhibit gastric motility. Their central activities include the promotion of REM sleep and an increase in cognitive function. The compounds of this invention are also remarkably reduced in size in comparison with the natural hormone and its peptide analogs such as octreotide and seglitide, which allows ease of formulation. Many of the instant compounds show activity following oral administration.

SUMMARY OF THE INVENTION

This invention relates to compounds which are agonists of somatostatin and selective toward somatostatin receptor subtype SSTR2. The compounds have a number of clinical uses including in the treatment and prevention of diabetes, cancer, acromegaly, depression, chronic atrophic gastritis, Crohn's disease, ulcerative colitis, retinopathy, arthritis, pain both viseral and neuropathic and to prevent restenosis. Many of the compounds are orally active. Thus, it is an object of this invention to describe such compounds. It is a further object to describe the specific preferred stereoisomers of the somatostatin agonists. A still further object is to describe processes for the preparation of such compounds.

Another object is to describe methods and compositions which use the compounds as the active ingredient thereof. Further objects will become apparent from reading the following description.

DETAIL DESCRIPTION OF THE INVENTION

The invention addresses a compound of structural formula I:

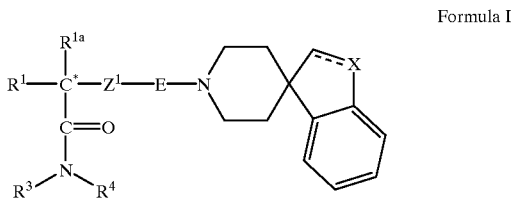

Formula I wherein:

the dotted line represents an optional bond;

$R^1$ is selected from the group consisting of: $C_1$–$C_6$ alkyl, aryl, aryl ($C_1$–$C_6$ alkyl), heteroaryl, heteroaryl ($C_1$–$C_6$ alkyl), ($C_3$–$C_7$ cycloalkyl)($C_1$–$C_6$-alkyl)—, ($C_1$–$C_5$ alkyl)—K—($C_1$–$C_5$ alkyl)—, aryl($C_0$–$C_5$ alkyl)—K—($C_1$–$C_5$ alkyl)—, and ($C_3$–$C_7$ cycloalkyl)($C_0$–$C_5$ alkyl)—K—($C_1$–$C_5$ alkyl)—, where K is —O—, —S(O)$_m$—, —N(R$^2$)C(O)—, —C(O)N(R$^2$)—, —CR$^2$=CR$^2$—, or —C≡C—, where R$^2$ and alkyl may be further substituted by 1 to 5 halogen, S(O)$^m$R$^{2a}$, 1 to 3 of OR$^{2a}$ or C(O)OR$^{2a}$, and aryl and heteroaryl are defined within, and where the aryl and heteroaryl are unsubstituted or substituted with a substitutent selected from: 1 to 3 of $C_1$–$C_6$ alkyl, 1 to 3 of halogen, 1 to 2 of —OR$^2$, methylenedioxy, —S(O)$_m$R$^2$, 1 to 2 of —CF$_3$, —OCF$_3$, nitro, —N(R$^2$)C(O)(R$^2$), —C(O) OR$^2$, —C(O)N(R$^2$)(R$^2$), —1H-tetrazol-5-yl, —SO$_2$N(R$^2$) (R$^2$), —N(R$^2$)SO$_2$ phenyl, or —N(R$^2$)SO$_2$R$^2$;

$R^2$ & $R^5$ are selected from hydrogen, $C_1$–$C_8$ alkyl, (CH$_2$)$_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or NR$^{3a}$, where R$^{3a}$ is hydrogen, or $C_1$–$C_6$ alkyl, optionally substituted by hydroxyl; aryl is defined within $R^{1a}$ is selected from the group consisting of hydrogen, and $C_1$–$C_3$ alkyl;

$R^{2a}$ is selected from the group consisting of hydrogen and $C_1$–$C_3$ alkyl, said alkyl optionally substituted by hydroxyl;

E is selected from the group consisting of —SO$_2$—, —CO (C(R$^2$)2)$_n$—, —C(=N—CN)—, —C(=N—NO$_2$)— and —C(=N—SO$_2$N(R$^2$)2)—;

$Z^1$ is —NR$^{2a}$;

$R^3$ is selected from the group consisting of H, $C_{1-8}$ alkyl, (CH$_2$)$_t$aryl and (CH$_2$)$_t$heteroaryl;

$R^4$ is CH(CO$_2$R$^2$)(CH$_2$)$_n$N(R$^2$)$_2$, CH(R$^2$)—(CH$_2$)$_n$N(R$^2$)$_2$, CH(CO$_2$R$^2$), CHCON(R$^2$)$_2$, CH(CO$_2$R$^2$)CH$_2$W(CH$_2$)$_n$N (R$^2$)$_2$,

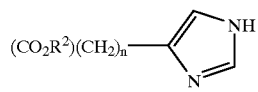

or $R^6$ $R^6$ is:

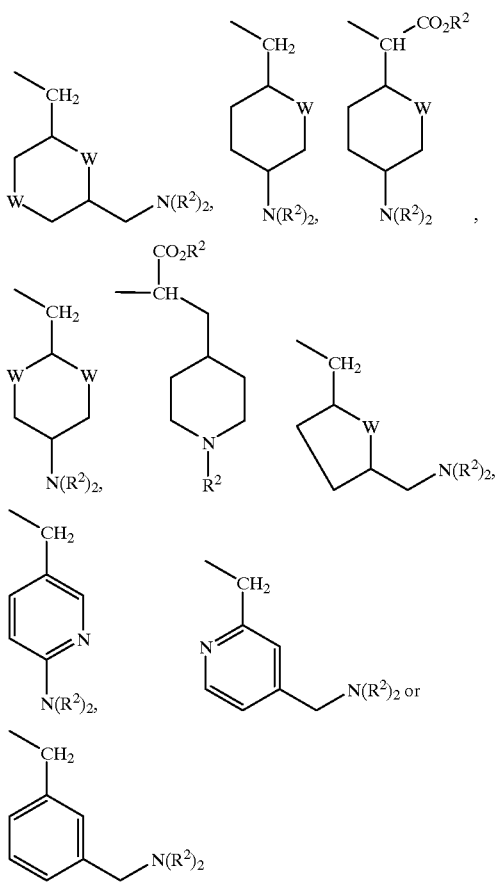

wherein $R^6$ is optionally substituted with 1 to 3 groups of $R^2$, 1 to 3 of halogen, 1 to 2 of —$OR^2$, methylenedioxy, —$S(O)_mR^2$, 1 to 2 of —$CF_3$, —$OCF_3$, —$N(R^2)C(O)(R^2)$, —$C(O)OR^2$, —$C(O)N(R^2)(R^2)$, —$SO_2N(R^2)(R^2)$, —$N(R^2)SO_2$ phenyl, or —$N(R^2)S_2R^2$;

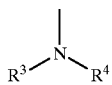

can be

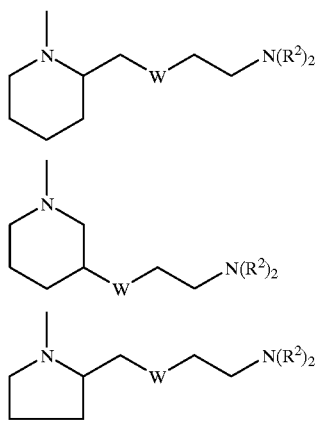

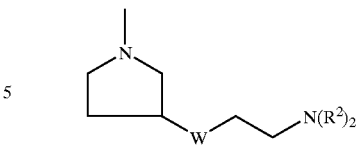

when the dotted line does not represent a bond, X is selected from the group consisting of $CH_2$, $CHCO_2R_2$, $C(O)$, $CHCH_2CO2R^2$, $CHCON(R^2)_2$ and $NSO_2R^2$, and when the dotted line represents a bond, X represents C substituted with $R^5$;

W is selected from the group consisting of O, S, $CH_2$, $N(R^2)C(O)$ and $C(O)N(R^2)$;

m is an integer from 0 to 2;

n is an integer from 0–5; and t is an integer from 0 to 3.

More particularly, the compounds and their pharmaceutically acceptable salts of the present invention are those of the general structural formula Ia or Ib:

Formula Ia

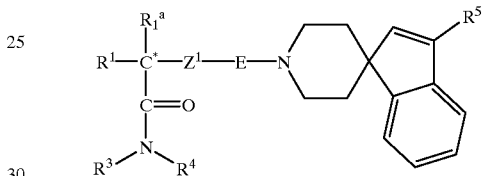

Formula Ib

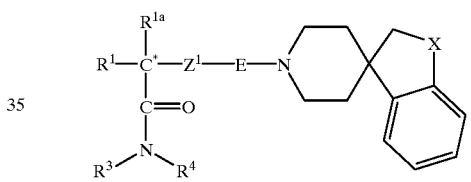

wherein:

$R^1$ is selected from the group consisting of: $C_1$–$C_6$ alkyl, aryl, aryl ($C_1$–$C_6$ alkyl), heteroaryl, heteroaryl ($C_1$–$C_6$ alkyl), ($C_3$–$C_7$ cycloalkyl)($C_1$–$C_6$ alkyl)—, ($C_1$–$C_5$ alkyl)—K—($C_1$–$C_5$ alkyl )—, aryl($C_0$–$C_5$ alkyl)—K—($C_1$–$C_5$ alkyl)—, and ($C_3$–$C_7$ cycloalkyl)($C_0$–$C_5$ alkyl)—K—($C_1$–$C_5$ alkyl)—, where K is —O—, —S(O)—, —$N(R^2)C(O)$—, —$C(O)N(R^2)$—, —$CR^2$=$CR^2$—, or —C≡C—, where $R^2$ and alkyl may be further substituted by 1 to 5 halogen, $S(O)_mR^{2a}$, 1 to 3 of $OR^{2a}$ or $C(O)OR^{2a}$, and aryl and heteroaryl are defined within, and where the aryl and heteroaryl are unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO2R^2$;

$R^2$ & $R^5$ are selected from hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl; aryl is defined within $R^{1a}$ is selected from the group consisting of hydrogen, and $C_1$–$C_3$ alkyl;

$R^{2a}$ is selected from the group consisting of hydrogen and $C_1$–$C_3$ alkyl, said alkyl optionally substituted by hydroxyl;

E is selected from the group consisting of —SO$_2$—, —CO(C(R$^2$)2)$_n$—, —C(=N—CN)—, —C(=N—NO$_2$)— and —C(=N—SO$_2$N(R$^2$)2)—;

Z$^1$ is —NR$^{2a}$;

R$^3$ is selected from the group consisting of H, C$_{1-8}$ alkyl, (CH$_2$)$_t$aryl and (CH$_2$)$_t$heteroaryl;

R$^4$ is CH(CO$_2$R$^2$)(CH$_2$)$_n$N(R$^2$)$_2$, CH(R$^2$)—(CH$_2$)$_n$N(R$^2$)$_2$, CH(CO$_2$R$^2$), CHCON(R$^2$)$_2$, CH(CO$_2$R$^2$)CH$_2$W(CH$_2$)$_n$N(R$^2$)$_2$,

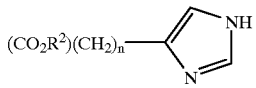

or R$^6$

R$^6$ is selected from the group consisting of:

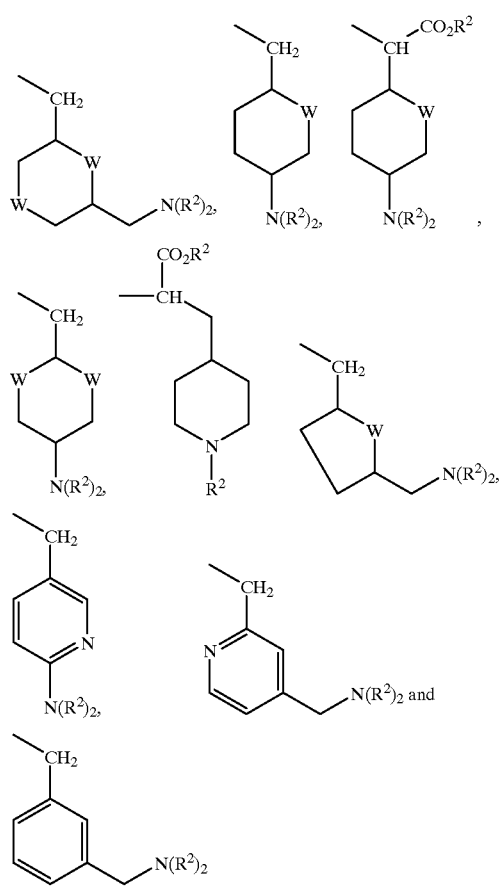

wherein R$^6$ is optionally substituted with 1 to 3 groups of R$^2$, 1 to 3 of halogen, 1 to 2 of —OR$^2$, methylenedioxy, —S(O)$_m$R$^2$, 1 to 2 of —CF$_3$, —OCF$_3$, —N(R$^2$)C(O)(R$^2$), —C(O)OR$^2$, —C(O)N(R$^2$)(R$^2$), —SO$_2$N(R$^2$)(R$^2$), —N(R$^2$)SO$_2$ phenyl, or —N(R$^2$)S$_2$R$^2$;

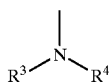

can be

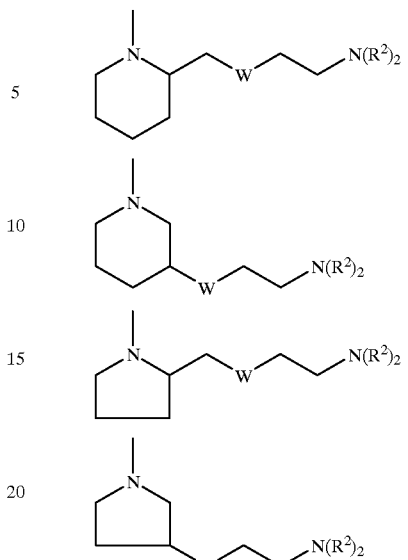

X is selected from the group consisting of CH$_2$, CHCO$_2$R$_2$, C(O), CHCH$_2$CO$_2$R$^2$, CHCON(R$^2$)$_2$ and NSO$_2$R$^2$;

W is selected from the group consisting of O, S, CH$_2$, N(R$^2$)C(O) and C(O)N(R$^2$);

m is an integer from 0 to 2;

n is an integer from 0–5, and t is an integer from 0 to 3.

Preferred compounds of the instant invention include those of Formula Ib-1 and Ib-2:

Formula Ib-1

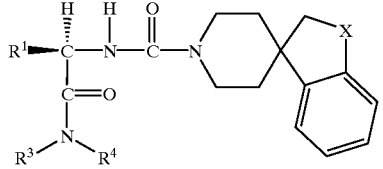

Formula Ib-2

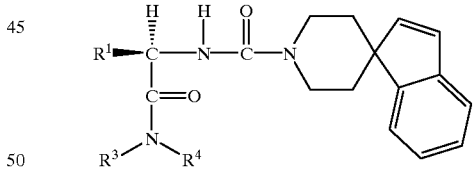

wherein:

R$^1$ is selected from the group consisting of: aryl (C$_1$–C$_6$ alkyl), heteroaryl(C$_1$–C$_6$ alkyl), where aryl and heteroaryl is selected from: phenyl, indanyl, benzyloxy, benzothiazolyl, biphenyl, aza-indolyl, benzyl(with 1,4-butane diamine) naphthyl, quinolinyl, indolyl, pyridyl, benzothienyl, benzofuranyl, thiazolyl, and benzimidazolyl, and where the aryl and heteroaryl are unsubstituted or substituted with a substitutent selected from: 1 to 3 of C$_1$–C$_6$ alkyl, 1 to 3 of halogen, 1 to 2 of —OR$^2$, 1 to 2 of —CF$_3$, —OCF$_3$, nitro, C(O)OR$^2$, or —C(O)N(R$^2$)(R$^2$);

R$^2$ is selected from: hydrogen, C$_1$–C$_8$ alkyl, and (CH$_2$)$_t$ aryl, where two C$_1$–C$_6$ alkyl groups are present on one atom, they optionally are joined to form a C$_3$–C$_8$ cyclic ring, optionally including oxygen, sulfur or NR$^{3a}$, where R$^{3a}$ is hydrogen, or C$_1$–C$_6$ alkyl, optionally substituted by hydroxyl;

R$^3$ is selected from the group consisting of hydrogen, C$_1$–C$_8$ alkyl and (CH$_2$)$_t$ aryl;

R$^4$ is CH(CO$_2$R$^2$)(CH$_2$)$_n$N(R$^2$)$_2$, CH(R$^2$)—(CH$_2$)$_n$N(R$^2$)$_2$, CH(CO$_2$R$^2$), CHCON(R$^2$)$_2$, CH(CO$_2$R$^2$)CH$_2$W(CH$_2$)$_n$N(R$^2$)$_2$,

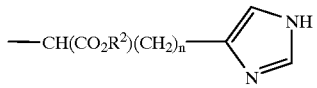

or R$^6$

R$^6$ is

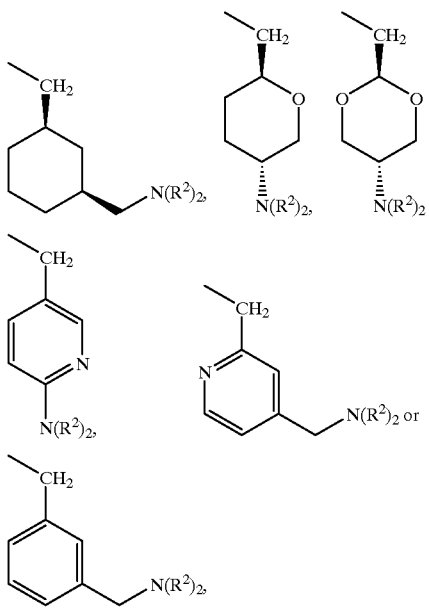

wherein R$^6$ is optionally substituted with 1 to 3 groups of R$^2$, 1 to 3 of halogen, 1 to 2 of —OR$^2$, methylenedioxy, —S(O)$_m$R$^2$, 1 to 2 of —CF$_3$, —OCF$_3$, —N(R$^2$)C(O)(R$^2$), —C(O)OR$^2$, —C(O)N(R$^2$)(R$^2$), —SO$_2$N(R$^2$)(R$^2$), —N(R$^2$)SO$_2$ phenyl, or —N(R$^2$)S$_2$R$^2$;

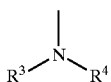

can be

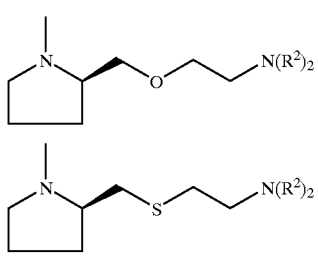

X is selected from the group consisting of CH$_2$, and NSO$_2$R$^2$;

and all other variables are described above.

More preferred compounds of Formula Ib-1 and Ib-2 are realized when:

R$^1$ is

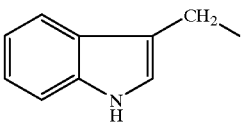

or

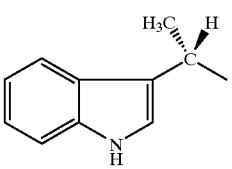

which may be substituted by 1 to 3 of R$^2$, 1 to 3 of halogen, 1 to 2 of —OR$^2$, 1 to 2 of —CF$_3$, —OCF$_3$, nitro, —C(O)OR$^2$, —C(O)N(R$^2$)(R$^2$);

R$^3$ is selected from hydrogen or methyl;

R$^4$ is CH(CO$_2$But)(CH$_2$)$_4$NH$_2$, CH(R$^2$)—(CH$_2$)$_4$NH$_2$, CH(CO$_2$But)CH$_2$WCH$_2$CH$_2$NH$_2$, or R$^6$ wherein R$^6$ is

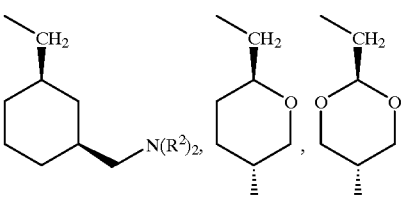

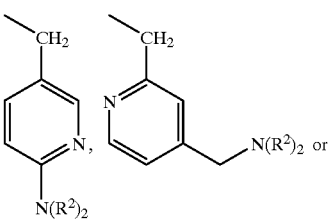

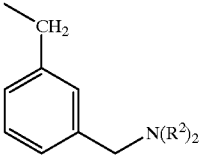

which is optionally substituted with 1 to 3 groups of R$^2$, 1 to 3 of halogen, 1 to 2 of—OR$^2$, 1 to 2 of—CF$_3$);

X is selected from the group consisting of CH$_2$, and NSO$_2$CH$_3$;

and all other variables are described above.

Also included in the invention is a pharmaceutical composition which is comprised of a compound of formula I in combination with a pharmaceutically acceptable carrier.

The invention also includes a method of treating diabetes, cancer, acromegaly chronic atrophic gastritis, Crohn's disease, ulcerative colitis, retinopathy, arthritis, viseral and neuropathic pain and to prevent restenosis, which comprises administering to a person or animal a compound of formula I in an amount which is effective for treating said disease or condition.

The invention is described herein in detail using the terms defined below unless otherwise specified.

The term "alkyl" refers to a monovalent alkane (hydrocarbon) derived radical containing from 1 to 15 carbon atoms unless otherwise defined and if two carbon atoms or more they may include a double or a triple bond. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

and
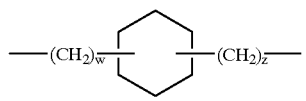

wherein: x plus y=from 0–10 and w plus z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

Aryl refers to aromatic rings e.g., phenyl, substituted phenyl and like groups as well as rings which are fused, e.g., naphthyl, indaryl, biphenyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted with from 1 to 3 groups of $C_1$–$C_{15}$ alkyl, halogen, —$OR^2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, —1H-tetrazol-5-yl, —$SO_2N(R^2)_2$, —$N(R^2)SO_2$ phenyl or —$N(R^2)SO_2R^2$. Preferred substituted aryls include phenyl and naphthyl substituted with one or two groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups selected from 1 to 3 of $C_1$–$C_8$ alkyl, halogen, —$OR^2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, —1H-tetrazol-5-yl, —$SO_2N(R^2)_2$, —$N(R^2)SO_2$ phenyl or —$N(R^2)SO_2R^2$.

Heteroaryl thus includes aromatic and partially aromatic groups which contain one or more heteroatoms. Examples of this type are thiophene, oxadiazole, imidazopyridine, pyridine, oxazole, thiazole, pyrazole, tetrazole, imidazole, pyrimidine, pyrazine, benzothienyl, benzofuranyl, indolyl, azaindole, benzimidazolyl, quinolinyl, isoquinolinyl and triazine.

The terms "heterocycloalkyl" and "heterocyclyl" refer to a cycloalkyl group (nonaromatic) in which one of the carbon atoms in the ring is replaced by a heteroatom selected from O, S, SO, $SO_2$ or N, and in which up to three additional carbon atoms may be optionally replaced by heteroatoms.

Heterocyclyl is carbon or nitrogen linked; if carbon linked and contains a nitrogen, then the nitrogen may be substituted by $R^{20}$. Examples of heterocyclyls are piperidinyl, morpholinyl, pyrrolidinyl, tetrahydrofuranyl, tetrahydroimidazo[4,5-c]pyridinyl, imidazolinyl, piperazinyl, pyrolidin-2-onyl, piperidin-2-onyl and the like.

Certain of the above defined terms may occur more than once in the above formula and upon such occurrence each term shall be defined independently of the other.

Salts encompassed within the term "pharmaceutically acceptable salts" refer to non-toxic salts of the compounds of this invention which are generally prepared by reacting the free base with a suitable organic or inorganic acid. Representative salts and esters include the following:

Acetate, Benzenesulfonate, Benzoate, Bicarbonate, Bisulfate, Bitartrate, Borate, Camsylate, Carbonate, Citrate, Dihydrochloride, Edetate, Edisylate, Estolate, Esylate, Fumarate, Gluconate, Glutamate, Hydrobromide, Hydrochloride, Hydroxynaphthoate, Lactate, Lactobionate, Laurate, Malate, Maleate ,Mandelate, Mesylate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Tosylate, and Valerate.

The compounds of the present invention may contain one or more asymmetric carbon atoms and may exist in racemic and optically active forms. All of these compounds are contemplated to be within the scope of the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention. In the case of the asymmetric carbon atom represented by an asterisk in Formula Ia and Ib, it has been found that compounds are more active as somatostatin agonists and, therefore preferred, in which the nitrogen substituent is above and the $R^{1a}$ is below the plane of the structure. An equivalent representation places $R^1$ and the N-substitutent in the plane of the structure with the C=O group above. This configuration corresponds to that present in a D-amino acid. In most cases, this is also designated an R-configuration, although this will vary according to the value of $R^1$ used in making R- or S-stereochemical assignments. In addition, configurations of some of the most preferred compounds of this invention are indicated. When the carbon atom in Formula Ia or Ib bearing an asterisk is of a defined and usually a D-configuration, up to two times more diastereomers result with each additional stereo centers are present. These diastereomers are arbitrarily referred to as diastereomer 1 ($d_1$) and diastereomer 2 (d2) and so on as so forth in this invention and, if desired, their independent syntheses or chromatographic separations may be achieved as described herein. Their absolute stereochemistry may be determined by the x-ray crystallography of crystalline products or crystalline intermediates which are derivatized, if necessary, with a reagent containing an asymmetric center of known absolute configuration.

The term "pharmacologically effective amount" shall mean that amount of a drug or pharmaceutical agent that will elicit the biological or medical response of a tissue, system, animal or human that is being sought by a researcher or clinician.

The term "substituted" shall be deemed to include multiple degrees of substitution by a named substitutent.

Where multiple substituent moieties are disclosed or claimed, the substituted compound can be independently substituted by one or more of the disclosed or claimed substituent moieties, singlely or plurally.

The ability of the compounds of the present invention to act as somatostatin agonists makes them useful as pharmacologic agents for mammals, especially for humans, for the treatment and prevention of disorders wherein somatostatin itself or the hormones it regulates may be involved. Examples of such disorders have been noted earlier and include diabetes, acromegalym neuropathic pain, restenosis, retinopathy, depression, arthritis and cancer. The instant compounds can also be used in combination with other therapeutic agents which are useful in treating these conditions. For example, for diabetes treatment these agents include metformin or other biguanides, acarbose, sulfonylureas, thiazolidinediones or other insulin sensitizers including, but not limited to, compounds which function as agonists on peroxisome proliferator-activated receptor gamma (PPAR-gamma), insulin, insulin-like-growth factor I, glucagon-like peptide I-glp-I and available satiety-promoting agents such as dexfenfluramine.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Intravenous dosages or oral dosages of the compounds of the present invention, when used for the indicated effects, will range between about 0.001 to 5 mg/kg and 0.1 to 50 mg/kg, respectively. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Throughout the instant application, the following abbreviations are used with the following meanings:

| | |
|---|---|
| Bu | butyl |
| Bn | benzyl |
| BOC, Boc | t-butyloxycarbonyl |
| BOP | Benzotriazol-1-yloxy tris/dimethylamino)-phosphonium hexafluorophosphate |
| calc. | calculated |
| CBZ, Cbz | Benzyloxycarbonyl |

-continued

| | |
|---|---|
| CDI | N,N'-carbonyl diimidazole |
| DCC | Dicyclohexylcarbodiimide |
| DCM | dichloromethane |
| DIEA | diisopropylethylamine |
| DMF | N,N-dimethylformamide |
| DMAP | 4-Dimethylaminopyridine |
| DSC | N,N'-disuccinimidyl carbonate |
| EDC | 1-(3-dimethylaminopropyl)-3-ethylcarbodi-imide hydrochloride |
| EI-MS | Electron ion-mass spectroscopy |
| Et | ethyl |
| EtOAc | ethyl acetate |
| EtOH | ethanol |
| eq. | equivalent(s) |
| FAB-MS | Fast atom bombardment-mass spectroscopy |
| HOAc | acetic acid |
| HOBT, HOBt | Hydroxybenztriazole |
| HPLC | High pressure liquid chromatography |
| KHMDS | Potassium bis(trimethylsilyl)amide |
| LAH | Lithium aluminum hydride |
| LHMDS | Lithium bis(trimethylsilyl)amide |
| Me | methyl |
| MeOH | methanol |
| MF | Molecular formula |
| MHz | Megahertz |
| MPLC | Medium pressure liquid chromatography |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Trimethylsilane |

The instant compounds can be effective to inhibit the secretion of various hormones and trophic factors in mammals. They may be used to suppress certain endocrine secretions, such as GH, insulin, glucagon and prolactin, in the treatment of disorders such as acromegaly; endocrine tumors such as carcinoids, vipomas, insulinomas and glucagonomas; or diabetes and diabetes-related pathologies, including retinopathy, neuropathy and nephropathy. The compounds may also be used to suppress exocrine secretions in the pancreas, stomach and intestines, for treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the instant compounds include cancers of the breast, prostate, and lung (both small cell and non-small cell epidermoids), as well as hepatomas, neuroblastomas, colon and pancreatic adenocarcinomas (ductal type), chondrosarcomas, and melanomas, and also atherosclerosis associated with vascular grafts and restenosis following angioplasty. Somastostatin in the brain inhibits the neuronal release of substance P(NK-1) and NK-1 antagonists have been shown to have a marked use as an antidepressant agent. Accordingly, the instant compounds are also useful in treating depression.

The compounds of the instant invention are further useful to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; and allergies, including asthma. The compounds can also function as neuromodulators in the central nervous system, with useful applications in the treatment of Alzheimer's disease and other forms of dementia, pain (as a spinal analgesic), and headaches. Furthermore, in disorders involving the splanchnic blood flow, including cirrhosis and oesophagal varices, the compounds of the invention can provide cytoprotection.

The preparation of compounds of Formula Ia or Ib of the present invention may be carried out in sequential or convergent synthetic routes. The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The phrase "mixed urea formation" refers to conversion of two different amines to form their mixed urea by using phosgene or equivalents such as CDI, DSC, or p-nitrophenyl chloroformate. The reaction involves reacting one amine first with the phosgene or equivalents in the presence of a base such as NMM, TEA or DIEA in a inert solvent such as dichloromethane, THF and DMF or mixtures thereof, followed by addition of the second amine and a base such as NMM, TEA or DIEA. The uses of protective groups for amines and carboxylic acids to facilitate the desired reaction and minimize undesired reactions are well documented. Conditions required to remove protecting groups which may be present can be found in Greene, T, and Wuts, P. G. M., *Protective Groups in Organic Synthesis*, John Wiley & Sons, Inc., New York, N.Y. 1991. CBZ and BOC were used extensively and their removal conditions are known to those skilled in the art. For example, removal of CBZ groups can be achieved by a number of methods such as catalytic hydrogenation in the presence of a noble metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethyl sulfide. Removal of BOC protecting groups is carried out in a solvent such as methylene chloride, methanol or ethyl acetate, with a strong acid, such as trifluoroacetic acid, hydrochloric acid or hydrogen chloride gas.

The protected amino acid derivatives required in the synthesis of compounds of Formula Ia or Ib are, in many cases, commercially available, where the protecting group ($P^1$) is, for example, methyl, allyl or benzyl groups. Other protected amino acid can be prepared by literature methods (Williams, R. M. *Synthesis of Optically Active α-Amino Acids*, Pergamon Press: Oxford, 1989). Many of the piperidines of Formula 2 are either commercially available or known in the literature and others can be prepared following literature methods described for analogous compounds. Some of these methods are illustrated in the subsequent schemes. Purification procedures include crystallization, normal phase or reverse phase chromatography.

The compounds of the present invention can be prepared readily according to the following Schemes or modifications thereof using readily available starting materials, reagents and conventional synthesis procedures. In these reactions, it is also possible to make use of variants which are themselves known to those of ordinary skill in this art, but are not mentioned in greater detail. The definition for $R^1$, $R^{1a}$, $R^2$, $R^3$, $R^4$, $R^5$, $Z^1$, W, E, etc., is described above unless otherwise stated.

SCHEME 1

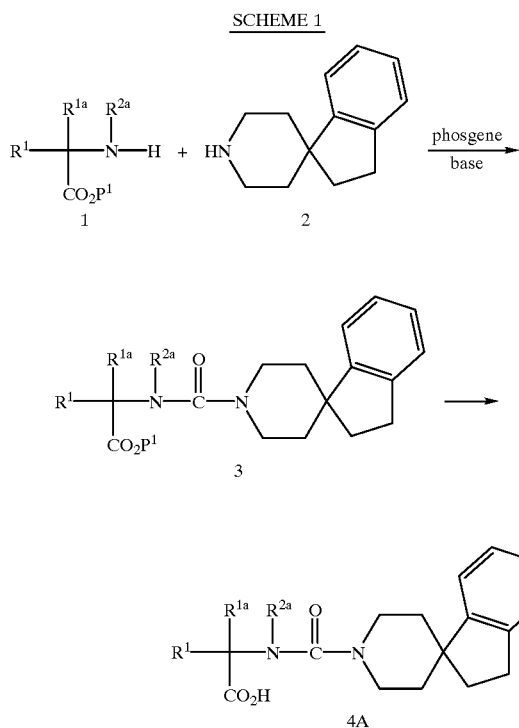

Intermediates of Formula 4A can be synthesized as described in Scheme 1. Mixed urea formation between the protected amino acid 1 and the piperidine of Formula 2, is conveniently carried out under usual urea formation reactions use phosgene or equivalents such as CDI, DSC, or p-nitrophenyl chloroformate. Removal of the $P^1$ protecting group can be achieved by saponification for most esters, or by catalytic hydrogenolysis when is $P^1$ benzyl, or by palladium (0) based homogeneous catalysis when $P^1$ is allyl. Intermediate 4A can be used as a common intermediate for the synthesis of somatostatin agonists with variation of the rest of the molecule of Formula I as shown in Scheme 2.

SCHEME 1A

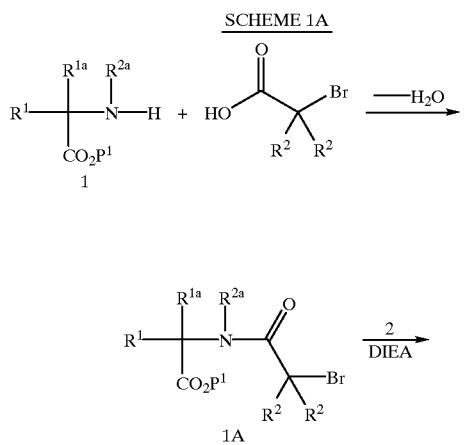

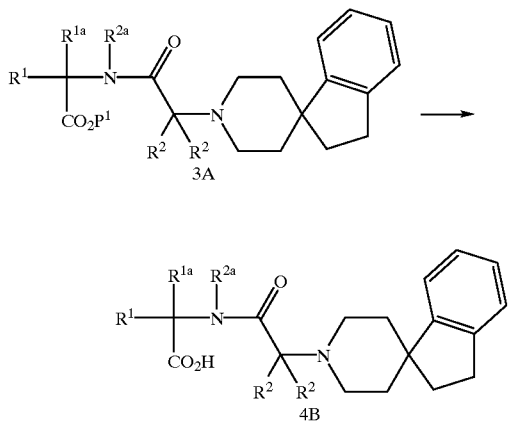

The preparation of amide intermediates of formula 4B can be achieved as shown in Scheme 1A. Standard peptide coupling reactions of protected amino acid 1 with 2-halo acids such as 2-bromoacetic acid gives intermediate 1A, which when reacted with amine of formula 2 gives the compound as 3A in the presence of a non-nucleophilic base such as DIEA. The P1 protecting group can be removed as described above.

SCHEME 2

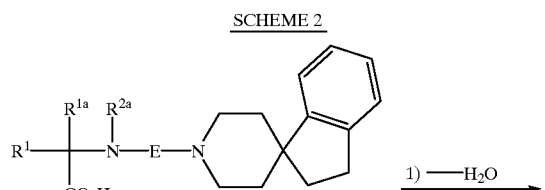

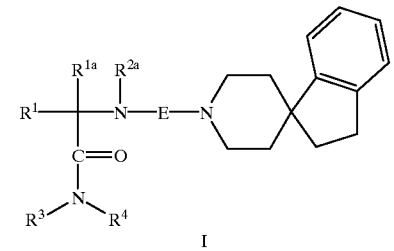

Intermediates of Formula 4 can be coupled to intermediates of formula 5 which is a properly mono protected with P2(such as BOC, Cbz, etc) diamine to afford compounds of Formula I under standard ester or peptide coupling reaction conditions.. Many of the selectively protected diamines of Formula 5 are either commercially available or known in the literature and others can be prepared following literature methods described for analogous compounds. Some of these methods are illustrated in subsequent schemes. The removal of protecting groups in can be carried out as noted above.

SCHEME 3

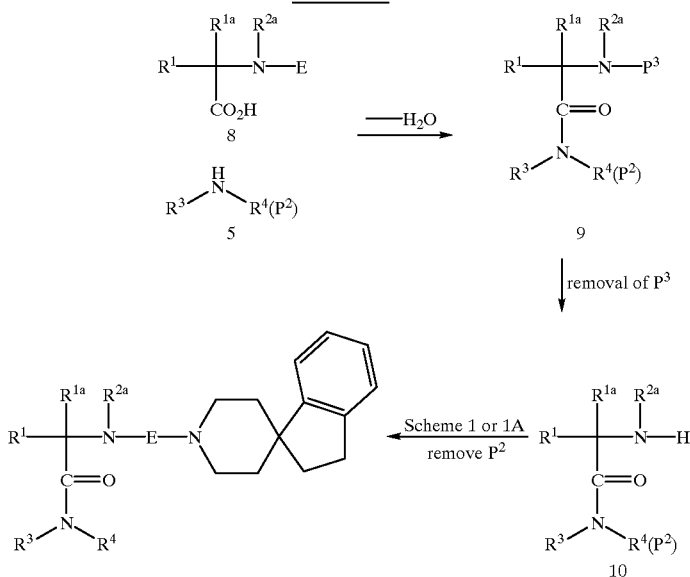

Alternatively, compounds of Formula I can be prepared starting from compound 5. The protected amino acid derivatives 8 are in many cases commercially available, where P3 is, for example, BOC, Cbz, Fmoc, and the like. N-Protected amino acid 8 can be coupled to intermediates of formula 5, wherein $Z^2$ is oxygen or substituted nitrogen to afford compounds of Formula 9 under standard ester or peptide coupling reaction conditions. The protecting group in compound 8 is selected with the criteria that its removal can be achieved without removing $P^2$. When the P2 protecting group is removed to afford compound 10, this compound can be further converted to compounds of formula I-A according to the procedures described in Scheme 1 and Scheme 1A.

General Procedure 1

Acid and amine coupling reaction to form amide: To a stirred solution of carboxylic acid (such as Intermediate 1), HOBT (1 equiv.) and the primary or secondary amine (such as intermediate 6, 1.2 equiv.) in dichloromethane (final concentration at about 0.2 M) at 0° C. was added EDC (1.5 equiv.). If the amine is in its hydrochloride form, 1.2 equiv. of DIEA was added. The reaction mixture was stirred at 0° C. for 4 hours, and then poured in to 3 N HCl. The organic layer was subsequently washed with aquous sodium bicarbonate and brine, dried and evaporated. Purification with silica chromatography give the desired product.

General Procedure 2

Urea formation between a primary amine and a piperidine. The primary amine (such as D-tryptophane methyl ester) was combined with disuccinimidyl carbonate (1–1.1 equiv.) and DIEA (2–3 equiv.) in dichloromethane. After stirring the reaction mixture for 0.5 h, during which time the reaction becomes clear, the piperidine (1.2 equiv.) along with DIEA (2 equiv.) were added and the mixture was permitted to stir over night. The reaction mixture was diluted with dichloromethane, and washed in succession with 1N HCl, saturated $NaHCO_3$ solution and brine, dried over $MgSO_4$, filtered and concentrated. The resulting crude product was purified by flash column chromatography.

General Procedure 3

Hydrogenolysis removal of Cbz: A mixture of the Cbz protected amine, 10% Palladium on carbon (5–10% weight of the Cbz compound) and 1 equiv. of HCl in ethanol is stirred under a hydrogen balloon for 2 hours. The mixture is filtered through celite and evaporated to afford the amine salt.

General Procedure 4

Hydrogenation of indene to indane: A mixture of the indene, 10% Palladium on carbon (5–10% weight of the Cbz compound) in ethanol is stirred under a hydrogen balloon for 2 hours. The mixture is filtered through celite and evaporated to afford the indane.

General Procedure 5

Saponification of esters: The ester was dissolved in THF, treated with LiOH (2.5 equiv.) in 1:1 EtOH/water and stirred for 4 h at room temperature. The pH was adjusted to ~2–3 by addition of 3N HCl and the resulting solution was extracted with ethyl acetate 3 times. The combined organic layers were washed with brine, dried over $MgSO_4$, filtered and concentrated to give the acid.

General Procedure 6

Removal of Boc protecting group: The Boc protected amine is dissolved in ethyl acetate, and two which HCl in dioxane (4 N, 4–10 equiv.) was added. The mixture was then stirred at room temperature for 4 hours or until the TLC indicates the complete disappearance of starting material. The mixture was then evaproated to dry to afford the amine hydrochloride salt.

INTERMEDIATE 1

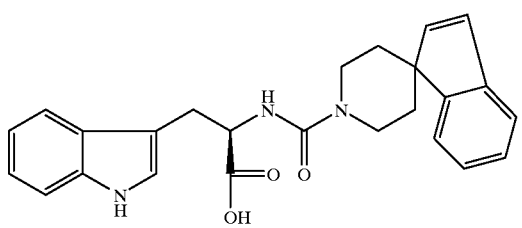

Step A

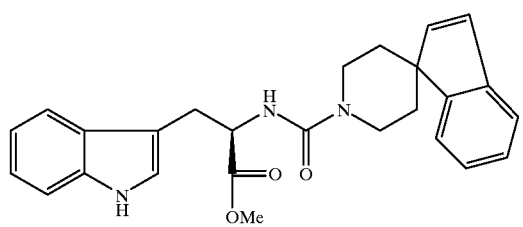

The intermediate was prepared using D-Trptophan methyl ester and spiro(indene-1,4'-piperidine) accoridng to the General procedure 2. ESI-MS calc. for$C_{26}H_{27}N_3O_3$: 429; Found: 430(M+H).

Step B

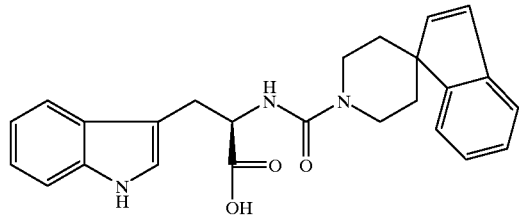

The intermediate was prepared using the methyl ester according to General procedure 5.

ESI-MS calc. forC25H25N3O3: 415; Found: 416(M+H).

INTERMEDIATE 1A

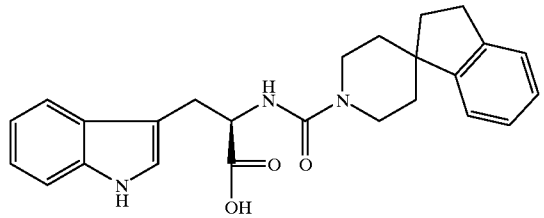

Hydrogenation of the Intermediate 1 according to the procedure of general procedure 4 gave the title compound.

ESI-MS calc. for C25H27N3O3: 417; Found 418 (M+H).

INTERMEDIATE 2

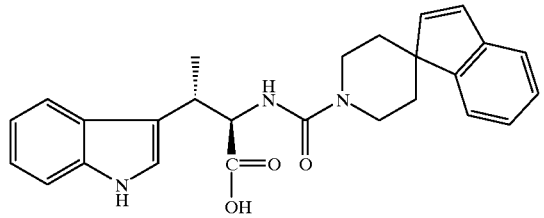

The compound was prepared according to General procedure 2 and 5 using (2R,3S)-β-Methyl-D-Tryptophan methyl ester and spiro(indene-1,4'-piperidine).

ESI-MS calc. forC26H27N3O3: 429; Found: 430(M+H).

INTERMEDIATE 2A

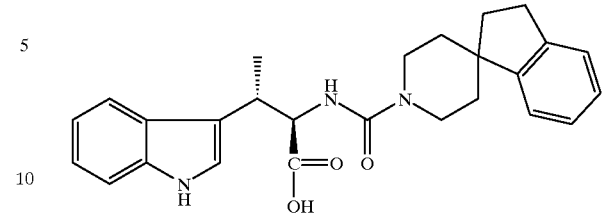

Intermediate 2 was converted to intermediate 2a accoring to the general procedure 4.

ESI-MS calc.for C26H29N3O3: 431; Found 432 (M+H).

INTERMEDIATE 3

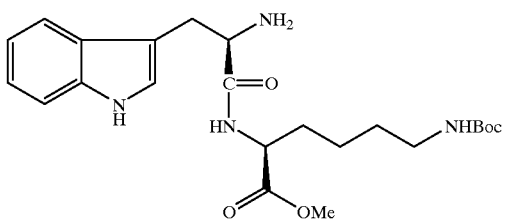

Step A

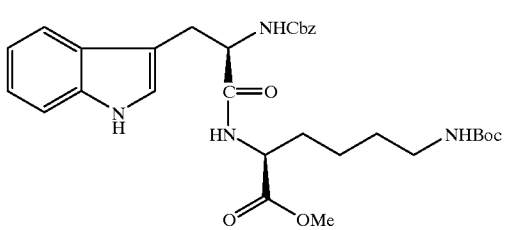

To a solution of commercially available N-Cbz-D-tryptophan (10.4 g, 30.6 mmol), N-ε-t-BOC-L-Lysine methyl ester hydrochloride (9.55 g, 32.2 mmol), HOBt (6.21 g, 46.0 mmol) and DIEA (5.61 mL, 32.2 mmol) in dichloromethane (100 mL) at 0° C. was added EDC (8.81 g, 46.0 mmol) in several portions over a 10 min period. The reaction mixture was allowed to warm to room temperature and stirred for 16 hrs. The reaction mixture was then poured into a saturated solution of NaHCO3 (100 mL), and the layers were separated. The organic layer was then sequentially washed with 100 mL portions of 1N HCl, water and brine, dried over anhydrous MgSO4, filtered and concentrated to give 17.8 g (100% crude yield) a yellow/white solid.

ESI-Mass calc. for C31H40N4O7; 580; found 581

Step B

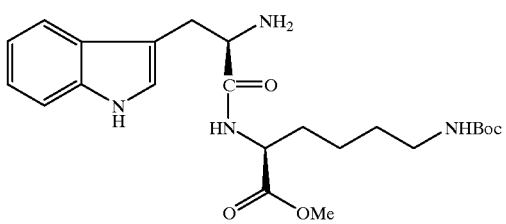

A mixture of the above product (17.8 g, 30.6 mmol) and Pearlman's catalyst [moist 20% Pd(OH)2 on carbon, 1.8 g)

in methanol (300 mL) was evacuated and purged with H₂ gas 3 times, then stirred at atmospheric pressure using a H₂ balloon for two hours. The reaction mixture was filtered through celite, TFA (3.5 g, 30.6 mmol) was added and the resulting solution was concentrated to give a white solid (16.3 g, 95% crude yield).
ESI-Mass cacl. for C23H34N4O5: 446; found 447

INTERMEDIATE 4

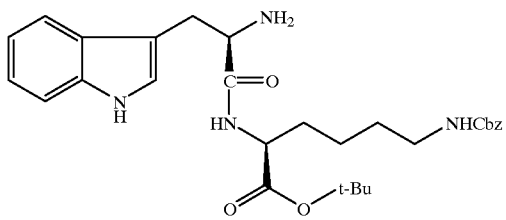

Step A

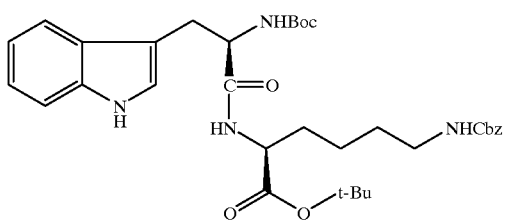

To a solution of commercially available N-BOC-D-Tryptophan (15.2 g, 50.0 mmol), N-ε-Cbz-L-Lysine t-butyl ester hydrochloride (18.7 g, 50.0 mmol), HOBt (6.76 g, 50 mmol) and DIEA (8.71 mL, 50.0 mmol) in dichloromethane (350 mL) at 0° C. was added EDC (12.5 g, 65.0 mmol) in portions over a 10 min period. After 30 min at 0° C. the reaction mixture was permitted to warm to room temperature and was stirred for an additional 4 h. The reaction mixture was then poured into water (300 mL), the phases were separated, and the organic layer was washed in turn with saturated NaHCO₃ (250 mL) and brine (250 mL), dried over anhydrous MgSO₄, filtered and concentrated. The crude product was purified by flash chromatography (silica, 50% ethyl acetate/hexane), furnishing 27.5 g (88% yield) of product as a white solid.

¹H NMR (CDCl₃, 400 MHz) δ9.12 (br s, 1H), 7.70 (d, J=6.8 Hz, 1H), 7.31–7.38 (m, 6H), 7.08–7.17 (m, 2 H), 6.97 (d, J=1.6 Hz, 1H), 5.96 (br s, 1H), 5.28 (br s, 1H), 5.13 (s, 2H), 4.94 (br s, 1H), 4.49 (br s, 1H), 4.31 (app br d, J=5.2 Hz, 1H), 3.22–3.30 (m, 1H), 3.03–3.13 (m, 2H), 2.93–3.02 (m, 1H), 1.70 (br s, 2H), 1.43 (br s, 9H), 1.35 (s, 9H), 0.64–0.85 (m, 2H).
ESI-MS calc. for C₃₄H₄₆N₄O₇: 622; Found 623 (M+H).
Step B

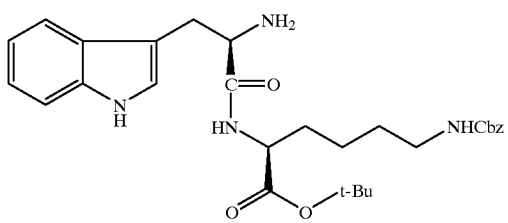

HCl gas was bubbled through a solution of the above product (10.0 g, 16.1 mmol) in ethyl acetate (75 mL) at 0°

C. for two min. The reaction mixture was stirred for an additional 10 min., then concentrated to give 8.64 g of a mixture (3:2) of desired product to a side product in which the t-butyl ester of the product had been hydrolyzed to the corresponding acid.
ESI-MS calc. for C₂₉H₃₈N₄O₅: 522; Found 523 (M+H).

INTERMEDIATE 5

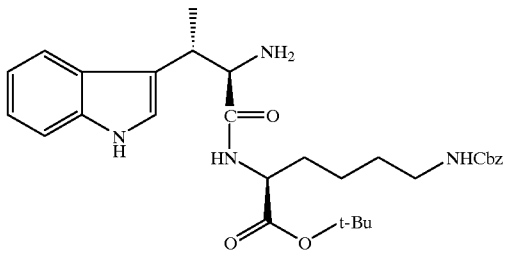

Step A

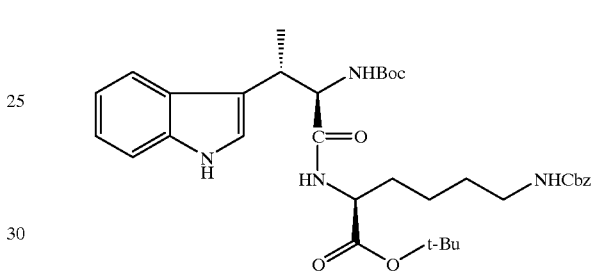

To a solution of (2R,3S)—N-BOC-β-methyl tryptophan (7.79 g, 24.5 mmol), N-ε-Cbz-L-lysine t-butyl ester hydrochloride (10.04 g, 26.9 mmol), HOBt (4.96 g, 36.7 mmol) and DIEA (4.69 mL, 26.9 mmol) in dichloromethane (150 mL) at 0° C. was added EDC (7.04 g, 36.7 mmol) in portions over a period of 10 min. The reaction mixture was allowed to warm to room temperature, stirred for 3.75 h, and poured into a saturated solution of NaHCO₃ (100 mL). The organic layer was separated and washed sequentially with 1N HCl (100 mL), water (100 mL), and brine (100 mL), then dried over anhydrous MgSO₄, filtered and concentrated to give 14.5 g (93% crude yield) of a white/yellow solid.
ESI-MS calc. for C₃₅H₄₈N₄O₇: 636; Found 637 (M+H).
Step B

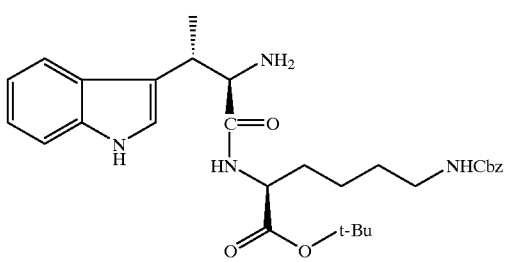

To a solution of the above adduct (554 mg, 0.870 mmol) in methanol (8 mL) was added methane sulfonic acid (251 mg, 2.61 mmol) and the resulting mixture was stirred at room temperature for 70 hrs. The reaction mixture was concentrated to remove the methanol, dissolved in dichloromethane (50 mL) and washed three times with 2N NaOH solution (40 mL), once with brine (40 mL) and dried over anhydrous MgSO₄, filtered and concentrated to give 280.1 mg (60% yield) of a white solid. HPLC analysis indicated 93% purity of the desired amine.

ESI-Mass calc. for $C_{30}H_{40}N_4O_5$: 536; Found 537 (M+H).

INTERMEDIATE 6

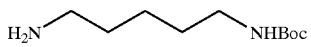

To a stirred solution of 1,5-pentadiamine (0.2 mole) in methanol (500 mL) was slowly added Boc2O (0.1 mole) in dichloromethane (100 mL). The mixture was stirred overnight, and evaporated to remove the solvents. The resulting residue was partitioned between water and dichloromethane. The organic layer was washed with brine, dried over Na2SO4 and evaporated to give the monoprotected amine, with some diBoc material which do not effect further reactions.

ESI-Mass calc for C10H22N2O2: 202; found 203 (M+1)

INTERMEDIATE 7

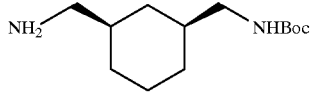

Step A

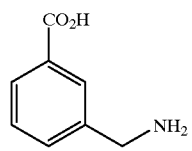

Commercially available m-cyanobenzoic acid (38 g, 0.26 mol) was dissolved in methanol (350 mL). Raney Ni (2 g) was added and 75 mL of $NH_3$ was condensed into the vessel. The resulting mixture was agitated at 80° C. under 1000 psi $H_2$ for 16 h. The mixture was filtered through celite and concentrated. The crude product was used in the following step.

Step B

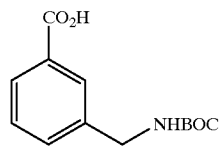

To the crude product from the above step (0.26 mol) was added a solution of NaOH (18.7 g, 0.468 mol) in water (200 mL). Then $BOC_2O$ (62 g, 0.28 mol) in p-dioxane (200 mL) was added via addition funnel over 0.5 h. After an additional 2 h the reaction mixture was concentrated to remove the dioxane and then washed twice with DCM (200 mL). The aqueous phase was acidified by slow addition of conc. HCl while cooling in an ice bath. Some gas evolution indicated the presence of residual Raney Ni. The aqueous mixture was then extracted twice with ether (200 mL). The combined ethereal extracts were washed with 1N HCl (200 mL), and brine (200 mL), dried over $MgSO_4$, filtered and concentrated to afford 33.3 g of a white solid.

Step C

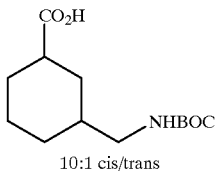

10:1 cis/trans

To a solution of the product from the previous step (10.0 g, 39.8 mmol) in glacial acetic acid (40 mL) was added $PtO_2$ and the resulting mixture was agitated under 50 psi $H_2$ for overnight. The reaction mixture was filtered through celite and the filter cake was futher washed with two portions of methanol (50 mL each). The filtrate was concentrated. The remaining acetic acid was removed by toluene/acetic acid azeotrope. The product (13.15 g) was collected as a white solid.

$^1$HNMR analysis indicated that the product was ≧10:1 cis/trans.

CI-MS calc. for C13H23NO4: 257; Found 258 (M+H).

Step D

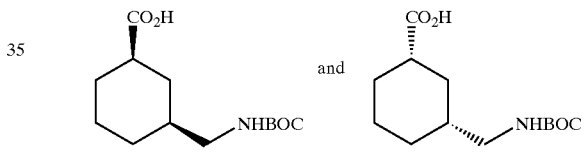

The racemic product of the above reaction (78 g, 0.30 mol) was combined with (S)-α-methylbenzylamine (39 mL, 0.30 mol) in hot ethyl acetate. Slow cooling to room temperature with gentle stirring and continued stirring overnight afforded crystals. The above was repeated four times (pure seed crystals from an earlier purification facilitated more efficient purification). The resulting salt was partioned between ethyl acetate and 3 N HCl. The organic layer was washed with brine, dried over $MgSO_4$, filtered and concentrated to afford 9.3 g of optically enhanced acid. The purity of the acid was found to be ≧20:1 by derivatization as described below. The absolute stereochemistry of both stereocenters was established by x-ray crystallographic analysis of the final pure (S)-α-methylbenzylamine salt (see below) as being (R) alpha to the carboxyl group and (S) alpha to the BOC-aminomethyl group. The combined mother liquors from the above purification were converted back to free acid as described above. Three recrystallizations of the acid recovered from the ML were carried out in the same fashion using (R)-α-methylbenzylamine to give (after extractive removal of the amine) 9.6 g of free acid of the opposite absolute stereochemistry as for the initial batch described above. Again, the purity was demonstrated to be ≧20:1 by $^1$H NMR analysis of a derivative.

Determination of Optical Purity

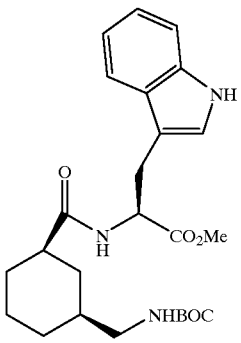

A small sample of the acid purified as described above (10.8 mg, 0.0420 mmol) was combined with H-Trp-OMe·HCl (14 mg, 0.055 mmol), EDC (12 mg, 0.063 mmol), HOBt (9.0 mg, 0.063 mmol) and DIEA (10 μL, 0.055 mmol) in DCM (1 mL). The resulting solution was allowed to stir at rt for 3 h at which time no acid starting material could be detected by TLC analysis. The reaction mixture was diluted with DCM (10 mL) and washed sequentially with 1 N HCl (3×5 mL), saturated NaHCO$_3$ solution (3×5 mL) and brine (5 mL), dried over MgSO$_4$, filtered and concentrated. $^1$H NMR analysis of the crude product indicated an isomer ratio of ~25:1 by integration of the singlet signals arising from the Lys-OMe group.

$^1$H NMR (CDCl$_3$, 400 MHz) 8.35 (br s, 1H), 7.50 (d, J=7.6 Hz, 1H), 7.35 (d, J=7.6 Hz, 1H), 7.17 (t, J=7.6 Hz, 1H), 7.09 (t, J=7.6 Hz, 1H), 6.94 (d, J=1.5 Hz, 1H), 5.95 (d, J=7.6 Hz, 1H), 4.91 (m, 1H), 4.59 (br s, 1H), 3.69 (s, 3H), 3.31 (dd, J=6.1, 15.2 Hz, 2H), 3.00 (m, 1H), 2.83 (m, 1H), 1.99 (m, 1H), 1.86–1.60 (m, 5H), 1.44 (s, 9H), 1.31–1.12 (m, 2H), 0.98 (q, J=11.4 Hz, 1H), 0.82 (m, 1H).

Step E

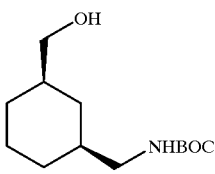

The pure (3S)-BOC-aminomethyl cyclohexane-(1R)-carboxylic acid (495 mg, 1.92 mmol) was dissolved in THF (5 mL), cooled to 0° C. and treated dropwise with a 2 M solution of BH3·DMS in THF (1.6 mL, 3.2 mmol). After an additional 5 min at 0° C. the temperature was permitted to warm to rt and the reaction mixture was stirred for 1.5 h. Water was then added dropwise to quench thew remaining borane. When gas evolution ceased the reaction mixture was diluted with ethyl acetate (75 mL) and washed sequentially with 1N HCl (50 mL), and brine (50 mL). The organic layer was dried over MgSO$_4$, filtered and concentrated to afford the crude product (534 mg) which was used without further purification. The alcohol of the opposite absolute stereochemistry was prepared in the same way.

$^1$H NMR (CDCl$_3$, 400 MHz) δ4.60 (br s, 1H), 3.42 (m, 2H), 2.94 (m, 2H), 1.82–1.68 (m, 5H), 1.48 (m, 1H), 1.41 (s, 9H), 1.23 (m, 1H), 0.82 (m, 2H), 0.58 (q, J=12.4 Hz, 1H).

Step F

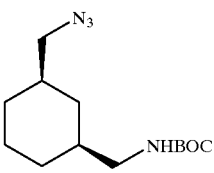

To a solution of the alcohol prepared as described above (445 mg, 1.83 mmol) in DCM (10 mL) at 0° C. was added triethylamine (510 μL, 3.66 mmol) and DMAP (ca. 50 mg, catalytic), followed in turn by methane sulfonyl chloride (160 μL, 2.01 mmol). After 1.5 h the reaction mixture was diluted with DCM (75 mL) and washed sequentially with 1N HCl (2×50 mL), saturated NaHCO$_3$ solution (2×50 mL), and brine (50 mL). The organic layer was dried over MgSO$_4$, filtered and concentrated to provide the mesylate product (594 mg) which was used immediately in the following reaction. A solution of the mesylate (590 mg, 1.83 mmol) and NaN$_3$ (238 mg, 3.66 mmol) in DMF (5 mL) was stirred at 65° C. for 7 h. The reaction mixture was diluted with ether (60 mL) and washed five times with water (40 mL each) and once with brine (40 mL). The ethereal layer was dried over MgSO$_4$, filtered and concentrated to give 422.7 mg of crude product. The azide of the opposite absolute stereochemistry was prepaed in the same fashion from the corresponding alcohol.

$^1$H NMR (CDCl$_3$, 400 MHz) δ4.58 (br s, 1H), 3.12 (dd, J=6.4, 1.6 Hz, 2H), 2.95 (m, 2H), 1.82–1.68 (m, 4H), 1.57 (m, 2H), 1.42 (s, 9H), 1.24 (m, 1H), 0.93–0.76 (m, 2H), 0.62 (q, J=12 Hz, 1H).

Step G

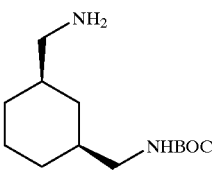

The intermediate prepared as described above (409 mg, 1.53 mmol) was combined with 10% Pd/C (80 mg) in methanol (12 mL). This mixture was stirred under a H$_2$ balloon for 6 h, then filtered through celite. The filter cake was washed with an additional 50 mL of methanol and the combined filtrates were concentrated. Flash chromatography (silica, 1.5% NH$_4$OH solution, 13.5% MeOH, 85% DCM) afforded the pure amine (264.1 mg). [α]$^{22}$D=−5.2° (c 0.78, CHCl$_3$).

$^1$H NMR (CDCl$_3$, 400 MHz) δ4.61 (br s, 1H), 2.93 (m, 2H), 2.50 (dd, J=6.4, 2.4 Hz, 2H), 1.80–1.66 (m, 4H), 1.50 (app br s, 2H), 1.40 (s, 9H), 1.25 (m, 2H), 0.79 (m, 2H), 0.52 (q, J=12.4 Hz, 1H).

INTERMEDIATE 8

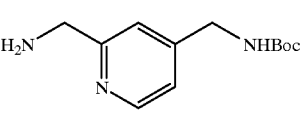

Step A: 4-(t-butyloxycarbonylaminomethyl)-pyridine N-oxide

To a stirred solution of 4-aminomethylpyridine (12.48 g, 0.115 mol) in dichloromethane (200 mL) at ambient temperature, was slowly added a solution of Boc2O (26.5 g, 1.05 equiv.) in dichloromethane (100 mL). The resulting mixture was stirred at room temperature for 4 hours, and then evaporated to remove solvents to afford 4-(t-butyloxycarbonylaminomethyl)-pyridine in quantitative yield. The residue was dissolved in acetic acid (30 mL) and hydrogen peroxide (30%, 13 mL) and the resulting solution was stirred at room temperature for one week. The reaction mixture was then evaporated and partition between 3N HCl and dichloromethane. The inorganic layer was extracted with dichloromethane five times and the extracts was combined and washed with small volume of sodium bicarbonate solution. The organic solution was dried and evaporated and purified by 5–10% methanol in dichloromethane to give the N-oxide (4.33 g).

$^1$H NMR (CDCl$_3$, 300MHz) 8.23 (d, J=7 Hz, 2H), 7.26 (d, J=7 Hz, 2H), 4.30 (d, J=5.6 Hz, 2 H); 1.44 (s, 9H). CI-MS calc. for C$_{11}$H$_{16}$N$_2$O$_3$:224; Found 225 (M+H), Step B: 4-(t-butyloxycarbonylaminomethyl)-2-cyano-pyridine To a stirred solution of the intermediate from the previous step (4.33 g, 19.3 mmol) and trimethylsilyl cyanide (3.35 mL, 1.3 equiv.) in dichloromethane (30 mL), was added dimethyl carbamyl chloride (2.3 mL, 1.3 equiv.) in 10 mL of dichloromethane at ambient temperature. After the reaction mixture had been stirred for one day, 20 mL of 10% potassium carbonate solution was added very slowly. The organic layer was separated and the aqueous layer was washed with dichloromethane twice. The combined organic extracts were dried and purified by silica gel chromatography eluting with 60% ethyl acetate in hexane to give the desired product (2.37 g). $^1$H NMR (CDCl$_3$, 300MHz) 8.65 (d, J=5 Hz, 1H), 7.61 (d, J=1 Hz, 1H), 7.42 (dd, J=1, 5 Hz, 1H), 5.10 (br.s, 1 H); 4.37 (d, J=6 Hz, 2H), 1.47 (s, 9H). CI-MS calc. for C$_{12}$H$_{15}$N$_3$O$_2$: 233; Found 234 (M+H), Step C: 2-aminomethyl-4-(t-butyloxycarbonylaminomethyl)-pyridine A solution of the intermediate from the previous step (1.37 g) and Raney Ni (1 g) in 20 mL of ethanol saturated with ammonia under 1000 psi of hydrogen, was stirred at 80° C. for 8 hours. The catalyst was removed by filtration and the solution was evaporated to give the desired compound (1.35 g) as a very thick oil. $^1$H NMR (CDCl$_3$, 300MHz) 8.40 (d, 3 Hz, 1H), 7.33 (s, 1H), 7.20 (d, J=3 Hz, 1 H), 4.27 (s, 2H), 3.88 (s, 2H), 1.45 (s, 9H).

INTERMEDIATE 8A

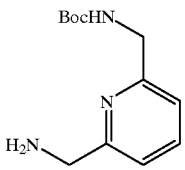

Prepared similarly from 2-aminomethylpyridine:

$^1$H NMR (CD$_3$OD, 400MHz) 7.74 (dd, J=7.80, 7.70 Hz, 1H), 7.26 (d, J=7.88 Hz, 1H), 7.22 (d, J=3 Hz, 1 H), 4.33 (s, 2H), 3.91 (s, 2H), 1.46–1.40 (m, 9H).

INTERMEDIATE 8B

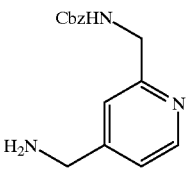

Step A: 4-(t-butyloxycarbonylaminomethyl)-2-(benzyloxycarbonylaminomethyl)-pyridine A mixture of 4-(t-butyloxycarbonylaminomethyl)-2-aminomethyl-pyridine(600 mg, 2.53 mmol), NMM (341 ml, 3.03 mmol), 4-DMAP ( 920 mg, 0.16 mmol) and benzyl chloroformate (433 ml, 3.30 mmol) in methylene chloride (15 ml) was stirred at room temperature overnight. The mixture was diluted with methylene chloride (50 ml) and then washed with water and saturated sodium bicarbonate. The organic layer was dried over sodium sulfate, filtered and evaporated in vacuo to give an oil. The crude product was purified by MPLC using 70% ethyl acetate in hexane as eluting solvent to give the title compound 844 mg (100%).
$^1$H NMR (CDCl3) d=1.45 (s, 3H), 4.25(br, 2H), 4.43 (d, J=5.7 Hz, 2H), 5.10 (s, 2H), 5.28 (br, 1H), 6.10 (br, 1H), 7.05 (d, J=5.1 HZ, 1 H), 7.11 (s, 1 H), 7.32 (m, 5H), 8.40 (d, J=5.1 Hz, 1H)

Step B: 4-aminomethyl-2-(benzyloxycarbonyl-aminomethyl)-pyridine

The 4-(t-butyloxycarbonylaminomethyl)-2-aminomethylpyridine (160 mg, 0.43 mmol) was dissolved in TFA (10 ml) and stirred at room temperature for two hours. The solvent was removed in vacuo. 163 mg of the crude product was collected and brought to next step reaction without further purification.

INTERMEDIATE 9

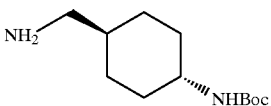

Step 1: N-(trans-4–Carboxycyclohexylmethyl)phthalimide

N-carboethoxyphthalimide (21.9 g, 0.10 mol), trans-4-(aminomethyl)cyclohexane carboxylic acid (15.7 g, 0.10 mol) and triethylamine (14 mL) were stirred in 100 mL THF and the mixture refluxed 18 hours. The nearly clear solution was poured into 400 ml water containing 10 mL glac. HOAc with rapid stirring and the precipitated product collected by suction and dried in a vacuum oven at 80° C.
mp 190–192°.

Step 2: N-(trans-4-Isocyanato-cyclohexylmethyl) phthalimide

The product from the previous step was stirred in 200 ml CCl$_4$ containing 10 mL SOCl$_2$ and the mixture refluxed under a drying tube until the solution remained clear on cooling and gas evolution ceased. The mixture was concentrated in vacuo to 100 ml and treated with 14.0 mL trimethylsilyl azide at reflux for 18 hours. The resulting solution was concentrated to give the crude title isocyanate.

Step 3: N-(4-tertbutoxycarbonylamino)cyclohexylmethyl phthalimide

The crude product from example 1, step 2 was treated with a solution of lithium tert butoxide in THF for 2 hours at room temperature to give a dark solution which was diluted with aqueous acetic acid and ice to precipitate the crude product which is recrystallized from 1-chlorobutane to give beige needles of the title urethane.

mp. 163–165°.

Step 4: N-(4-tertbutoxycarbonylamino)cyclohexylmethyl amine

The above urethane phthalimide was treated with 1 equivalent anhydrous hydrazine in isopropanol for 18 hours at room temperature followed by 4 hours reflux. The mixture was concentrated, diluted with cold aqueous acetic acid and filtered to remove phthalazinedione. The aqueous layer was basified with NaOH followed by extraction with ethyl acetate, drying, and evaporation to afford the desired product Intermediate as a solid.

INTERMEDIATE 10

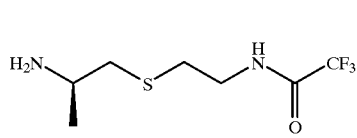

Step A

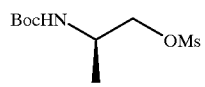

To a stirred solution of Boc-D-alaniol(1.0 g, 5.7 mmol) and DIEA (1.1 ml, 6.27 mmol) in dichloromethane (50 ml) at 0° C. was added ethylsulfonyl chloride (463ml, 5.98 mmol) slowly. The resulting mixture was stirred at room temperature for 60 min. TLC check showed the reaction completed and the reaction mixture was diluted with DCM and washed sequentially with 1N HCl and saturated NaHCO$_3$. Dried over Na$_2$SO$_4$, filtered and concentrated to give the crude product as an oil, which was used for next step reaction without further purification.

Step B

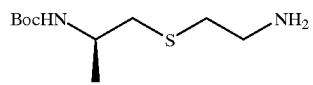

To a stirred solution of the crude product from the previous step and aminoethanethiol hydrochloride in THF-MeOH (4/1, 50 ml) was added NaOMe (1.5 equiv.) under nitrogen at 0° C. The resulting mixture was stirred under N$_2$ at room temperature for 60 min. The reaction was quenched by adding cold water. The reaction mixture was then evaporated and partitioned between water and DCM. The organic solution was dried over Na$_2$SO$_4$ and evaporated to dryness to give the crude product for next step without further purification.

Step C

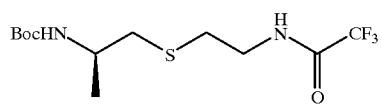

To a stirred solution of the intermediate from the previous step in THF (10 ml) was added ethyl trifluoroacetate (678ml, 5.7 mmol). The reaction mixture was stirred at room temperature for 30 min. The mixture was evaporated to dryness and purified by flash column chromatography(silica gel) using 40% EtOAc in hexane as an eluent. 650 mg desired product was collected with an overall yield of 35%.

Fab-MS calculated for C12H21N2O3F3S: 330, found 331 (M+H).

Step D

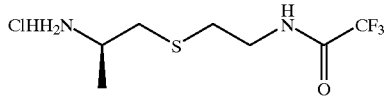

To the stirred solution of the intermediate from the previous step in ethyl acetate was bubbling HCl gas to saturation at 0° C. The mixture was stirred at room temperature for about five minutes. TLC check showed the reaction completed. The resulting solution was evaporated to dryness to give the desired product.

Mass (ESI) calculated for C7H13N2OF3S: 230; found 231 (M+H)

INTERMEDIATE 10A

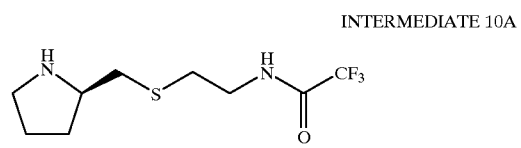

This compound was prepared similarly as Intermediate 9 but using Boc-D-prolinol at Step A instead.

ESI-Mass calc. for C9H15F3N2OS: 256; found 257

INTERMEDIATE 11

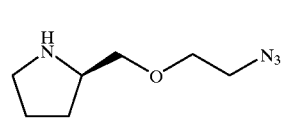

Step A

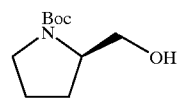

To a stirred solution of N-Boc-D-Pro-OH (10 g, 46.4 mmol) in dry THF(250 ml) at 0° C. was added dropwise BH3.Me2S (2M in THF, 41.8 ml, 83.5 mmol) through an addition funnel. The reaction mixture was stirred under nitrogen overnight. TLC check showed the reaction completed. The reaction was quenched by adding methanol through a addition funnel until the bubbling ceased. The solvent was removed in vacuo and the resulting oil was partitioned between ethyl acetate and brine solution and saturated NaHCO3 solution. The organic solution was dried over Na2SO4 and concentrated in vacuo to give the crude product 9.21 g. Mass (ESI) calc for C10H19NO3: 201; found 202 (M+H)

Step B

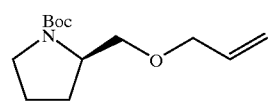

To a stirred solution of the intermediate from the previous step (5.0 g, 24.8 mmol) and allyl bromide (2.26 ml, 26.1 mmol) in THF at 0° C. was added NaH (60% in oil,1.04 g) in portion. The reaction mixture was slowly warmed-up to room temperature and was stirred overnight. The reaction was quenched with cold water (30 ml) and the mixture was extracted with ethyl acetate three times. The organic solutions were combined, dried over Na$_2$SO$_4$. and concentrated in vacuo to give the crude product 5.9 g. Mass (ESI) calc. for C13H23NO3: 241; found 242

Step C

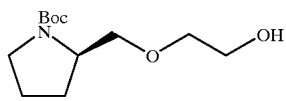

To a stirred solution of the intermediate from the previous step in ethanol (150 ml) at −78° C. was bubbling ozon until the reaction was completed (about 40 min, ,TLC monitored). After purged with N$_2$, a solution of NaBH$_4$ (1.82 g) in ethanol (50 ml) was added slowly at −78° C. Once the addition was done, removed the dryice-acetone bath and let the reaction stir overnight. Evaporated the mixutre to dryness and redissolved in ethyl acetate. To the above stirred mixture was added cold 1N HCl until the bubbling ceased. The mixture was extarcted with ethyl acetate for three times, and the organic phases were combined and dried over Na2SO4 and concentrated in vacuo to give the crude product 5.71 g as an oil. Mass (ESI) calc for C12H23NO4: 245; found 246

Step D

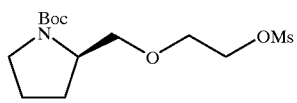

To a stirred solution of the intermediate from the previous step in DCM (200 ml) was added at 0° C. was added methylsulfonyl chloride (1.89 ml, 24.5 mmol) slowly. The resulting mixture was stirred at room temperature for 60 min. TLC check showed the reaction completed. Diluted with DCM and washed sequentially with 1N HCl and saturated NaHCO3. Dried over Na2SO4, filtered and concentrated to give the crude product as an oil, which was used for next step reaction without further purification.

Step E

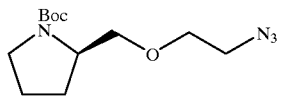

To a stirred solution of the intermediate from the previous step in DMF (150ml) was added water about 10 ml and sodium azide (5.98 g, 92 mmol). The reaction mixture was heated to 50° C. and stirred at this temperature for 4 hours. TLCV check showed the reaction completed. Afetr the reaction mixture cooled to room tempearture, about 100 ml water was added and extracted with ethyl acetate for three times, and the organic phases were combined and dried over Na2SO4. Chromatography purification (silica) using 35% ethyl acetate in hexane as an eluent provided the pure product 2.74 g. Mass (ESI) calculated for C12H22N4O3: 270; found 271

Step F

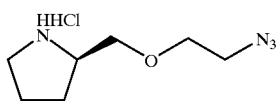

To the stirred solution of the intermediate from the previous step (1.265 g) in DCM(10 ml) was added 4N HCl in dioxane (10 ml) at room temperature. The mixture was stirred at room temperature for about 2 hours. TLC check showed the reaction completed. The resulting solution was evaporated to dryness to give the desired product. Mass (ESI) calculated for C7H14N4O: 170; found 171(M+H)

INTERMEDIATE 12

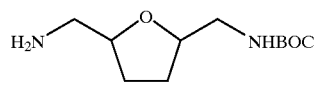

Step A: 2-(N-t-Butoxycarbonylaminomethyl)-5-hydroxymethyl tetrahydrofuran

2-Aminomethyl-5-hydroxymethyl tetrahydrofuran (2.4 g, 18 mmol) was dissolved in THF (40 mL) and treated with a solution of Boc2O (3.99 g, 18.3 mmol) in THF (20 mL) over about 10 min. The reaction mixture was stirred for 24 h and then concentrated to afford the BOC amino protected compound which was purified by MPLC (silica, 1% methanol/ethyl acetate).

Step B: 2-(N-t-Butoxycarbonylaminomethyl)-5-azidomethyl tetrahydrofuran

The product from the previous step (2.66 g, 11.5 mmol) was combined with triethyl amine (3.2 mL, 23 mmol) and DMAP (ca. 200 mg) in DCM (40 mL). The resulting solution was cooled to 0° C. and treated with MsCl (0.980 mL, 12.7 mmol), dropwise over 2 min. After 5 h the reaction mixture was diluted with DCM (75 mL) and washed with 1N HCl (75 mL), saturated NaHCO$_3$ solution (75 mL) and brine (75 mL). The organic layer was dried over MgSO$_4$, filtered and concentrated to afford 2.88 g of mesylate. The mesylate (2.87 g, 9.28 mmol) was combined with NaN$_3$ (1.21 g, 18.6 mmol) in DMF (30 mL) and heated at 70° C. for 15 h. The reaction mixture was diluted with ether (200 mL) and washed with water (5×100 mL) and brine (100 mL), dried over MgSO$_4$, filtered and concentrated to give 2.18 g of azide.

Step C: 2-(N-t-Butoxycarbonylaminomethyl)-5-aminomethyl tetrahydrofuran

The azide prepared in the previous step (2.0 g, 7.8 mmol) was dissolved in methanol (40 mL) and stirred under H$_2$ (1 atm) with Pd(OH)$_2$/C (200 mg, 20%) for 16 h. The reaction mixture was filtered through celite (filter cake was washed with additional methanol) and concentrated to give 1.77 g of the desired amine.

ESI-MS calc for C11H22N2O3: 230; Found 231 (M+H).

INTERMEDIATE 13

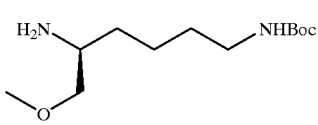

To a stirred solution of a—N-Boc-w-Cbz-lysinol (1 g, 2.7 mmol) and iodomethane (0.255 mL, 1.5 equiv.) in THF (100 mL) at 0° C. was slowly added sodium hydride (60% in mineral oil, 120 mg, 1.1 equiv.). The reaction mixture was allowed to warm to room temperature and stirred for 1 h. The mixture was queiched by adding sodium bicarbonate solution, and evaporated to remove THF. The residue was then partitioned between brine and ethyl acetate, and the organic layer was dried and evaporated. Purification with silica chromatography eluting with 50% ethyl acetate in hexane give the product (730 mg). The resulting material was then subjected hydrogenolysis removal of the Cbz group according to General Procedure 3 without the addition of HCl to give the title compound.

INTERMEDIATE 14

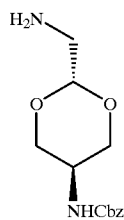

Step A

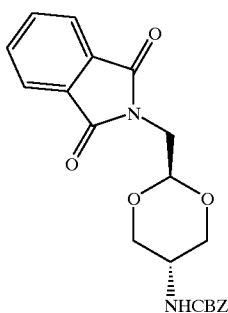

A stirred mixture of N-Cbz-serinol (497 mg, 2.21 mmol), (prepared using standard procedures from commercially available serinol oxalate and Cbz-Cl), phthalimidoacetaldehyde diethyl acetal (Aldrich, 581 mg, 2.21 mmol) and TsOH (21 mg, 0.11 mmol) in toluene (10 mL) was heated to reflux for 6 h. The resulting solution was cooled and evaporated in vacuo. Purification by flash chromatography (dry loaded on silica, 30% ethyl acetate/hexanes to 40% ethyl acetate/hexanes) afforded a 4:1 trans/cis mixture (107 mg) and a 1:4 trans/cis mixture (300 mg). The trans isomer was crystallized from absolute ethanol.

Step B

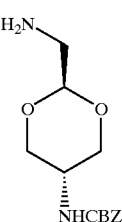

To a suspension of the product from the above reaction (106 mg, 0.268 mmol) in absolute ethanol was added hydrazine (1M solution in ethanol, 0.268 mmol) and the mixture was heated at reflux for 1 h. The resulting suspension was cooled and evaporated in vacuo. 2 M HCl (5 mL) was added and the mixture was warmed to 50° C. for 5 min. to give a suspension which was cooled and filtered. The solids were washed with more 2M HCl. The resulting solution was washed with DCM (2x) then basified with 50% NaOH solution (cooling in an ice bath), and the mixture was extracted with ethyl acetate (2x). The combined extracts were dried over $Na_2SO_4$, filtered and evaporated to give 57 mg of product as a waxy solid.

INTERMEDIATE 15

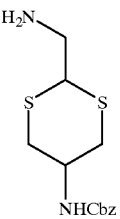

Step A

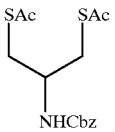

A stirred mixture of N-Cbz-serinol (31.5 g, 0.140 mol) (prepared using standard procedures from commercially available serinol oxalate and Cbz-Cl), and triphenylphosphine (80.7 g, 0.308 mol) in THF (500 mL) was cooled to 0° C. and treated with DEAD (48.5 mL, 53.6 g, 0.308 mol), followed by thiolacetic acid (22.0 mL, 23.4 g, 0.308 mol). The reaction mixture was stirred at 0° C. for two h then at rt overnight. Concentration of the reaction mixture was followed by flash chromatography (30–90% EtOAc/Hexanes gradient). The top fractions were crystallized from hot EtOAc/Hexanes (1:3), the crystalline side product was filtered off and the mother liquor was again subjected to flash chromatography, eluting with a 30–40% EtOAc/hexanes gradient to afford 25.7 g of pure product (54% yield).

$^1$H NMR (CDCl$_3$, 400 MHz) δ7.34–7.29 (m, 5H), 5.07 (s, 2H), 5.03 (d, J =8.0 Hz, 1H), 3.94 (m, 1H), 3.08 (d, J=5.60 Hz, 4H), 2.31 (s, 6H). ESI-MS calc for C15H19NO4S2: 341; Found 342 (M+H).

Step B

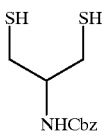

Methanol (500 mL) was deoxygenated by bubbling N$_2$(g) through it for 1 h. The bis-thiolester intermediate from the previous step 25.0 g, 73.2 mmol) was dissolved in the deoxygenated methanol, the resulting solution cooled to 0° C. and treated with sodium methoxide (8.90 g, 165 mmol). The reaction mixture was permitted to warm to rt and stir for an additional 1.25 h and then was concentrated under reduced pressure at 30° C. The residue was partitioned between deoxygenated EtOAc (as above) and 1 N HCl solution. The organic layer was washed with brine, dried over MgSO$_4$, filtered and concentrated to provide 18.3 g of crude product which required no additional purification (97% yield). $^1$H NMR (CDCl$_3$, 400 MHz) δ7.37–7.26 (m, 5H), 5.11 (s, 2H), 3.91 (m, 1H), 2.97–2.85 (m, 2H), 2.73 (dd, J=12.8, 8.4 Hz), 2.69 (dd, J=12.8, 8.4 Hz), 1.35 (d, J=12.4 Hz, 1H), 1.32 (d, J=12.8 Hz, 1H).

Step C

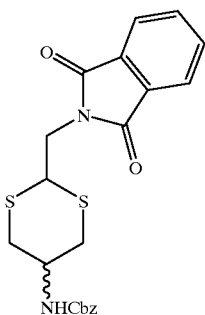

A stirred mixture of N-Cbz-thioserinol (911 mg, 3.54 mmol) and phthalimidoacetaldehyde (670 mg, 3.54 mmol, prepared from commercially available phthalimidoacetaldehyde diethyl acetal by heating in acetone with TsOH) in CH$_2$Cl$_2$ (10 mL) was cooled to 0° C. and treated with BF$_3$·OEt$_2$ (0.449 mL, 502 mg, 3.54 mmol). The resulting solution was warmed to rt and stirred overnight. The reaction mixture was diluted with CH$_2$Cl$_2$ and washed in turn with saturated NaHCO$_3$ solution, and brine. The organic layer was dried over MgSO$_4$, filtered and concentrated. Purification by MPLC, eluting with 55% EtOAc/hexanes, afforded 499 mg of a trans/cis mixture of the desired product (33% yield).
ESI-MS calc for C21H20N2O4S2: 428; Found 429 (M+H).

Step D

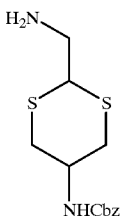

The product from Step C above (452 mg, 1.05 mmol) was dissolved in ethanol (10 mL) and treated with anhydrous hydrazine (51 mg, 1.58 mmol) at rt. The reaction mixture was stirred overnight and concentrated. The cis and trans isomers were separated by flash chromatography (1/9/90, NH$_4$OH/MeOH/CH$_2$Cl$_2$).

ESI-MS calc for C13H18N2O2S2: 298; Found 299 (M+H).

INTERMEDIATES 16 AND 17

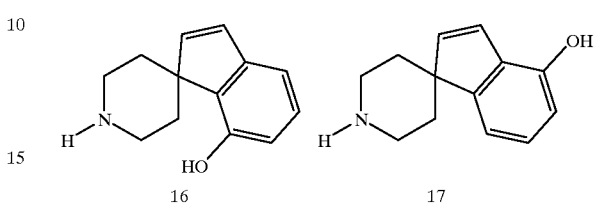

Step A

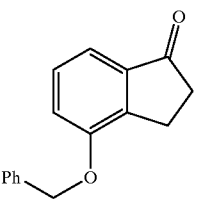

A stirred solution of 4-hydroxy indanone (20.0 g, 135 mmol), K$_2$CO$_3$ (37.3 g, 0.270 mol) and benzyl bromide (16.1 mL, 23.1 g, 135 mmol) in DMF (100 mL) was heated at 60° C. for 2 h. The reaction mixture was diluted with ether and water, the phases separated, and the aqueous phase washed two more times with ether. The ethereal layers were washed three times with water and once with brine. The ethereal phase was dried over MgSO$_4$, filtered, and concentrated to afford 32.1 g of crude product (100% yield).

ESI-MS calc for C16H14O2: 238; Found 239 (M+H).

Step B

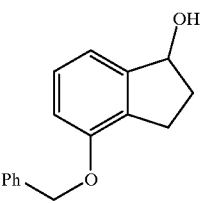

The product from Step A (30.9 g, 130 mmol) was dissolved in ethanol (400 mL) and treated with sodium borohydride (1.64 g, 43.2 mmol). After 3 h an additional portion of sodium borohydride (0.50 g, 13 mmol) was added and the reaction mixture was warmed at reflux for 20 min. The reaction mixture was cooled to 0° C. and quenched by slow addition of 3N HCl solution. The reaction mixture was concentrated and the resulting residue was partitioned between CH$_2$Cl$_2$ and 1 N HCl solution. The aqueous layer was extracted once more with CH$_2$Cl$_2$ and the combined organic layers were washed with brine, dried over MgSO$_4$, filtered and concentrated to afford 32.2 g of crude product.

ESI-MS calc for C16H16O2: 240; Found 241 (M+H).

Step C

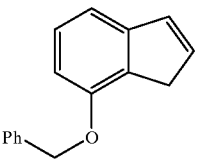

A toluene (300 mL) solution of the alcohol from Step B (30.7 g, 128 mmol) and toluenesulfonic acid (TsOH·H₂O, 1.0 g, 5.3 mmol) was heated at reflux for 1 h and then concentrated. The resulting residue was partitioned between CH₂Cl₂ and saturated NaHCO₃ solution. The aqueous layer was washed once more with CH₂Cl₂ and the organic layers were combined and washed with saturated NaHCO₃, then brine. The organic layer was dried over MgSO₄, filtered and concentrated to give 26.6 g of crude product (94% yield). ESI-MS calc for C16H14O: 222; Found 223 (M+H).

Step D

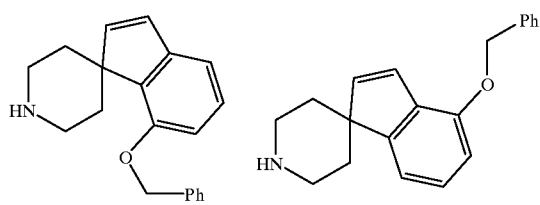

LHMDS (38.2 g, 0.229 mol) was combined in a dry vessel with 200 mL THF and cooled to −20° C. (ice/salt). The alkene prepared as described in Step C above (24.2 g, 0.109 mol) was slowly added in THF (100 mL) via addition funnel. The reaction micture was stirred for an addtional 1.5 h at ~5° C. and then N-BOC-bis-(2-chloroethyl) amine (26.4 g, 0.109 mol, prepared from bis-(2-chloroethyl) amine hydrochloride by standard reaction with BOC₂O and TEA) was added in THF (50 mL). The reaction mixture was warmed to rt and stirred overnight. Concentrated NH₄OH solution (7 mL) was added to quench any remaining alkyl halides and the mixture was stirred for an additional 4h. The reaction mixture was then diluted with ether and washed with 3N HCl solution (2×), saturated NaHCO₃ solution, and brine. The organic phase was dried over MgSO₄, filtered and concentrated. The crude product was purified by flash chromatography (5–15% EtOAc/hexanes) to afford 20.1 g of a mixture of isomers (47% yield). The BOC group was removed by dissolving the protected intermediate mixture in ether (200 mL) and bubbling HCl gas through this solution for 20 min. The resulting suspension was filtered and the collected white solid was stored under vacuum to afford 7.16 g of crude product (82% crude yield). The two isomers were separated by flash chromatography (0.8/7.2/92–1/9/90 gradient of NH₄OH/MeOH/CH₂Cl₂) to afford 4.47 g of the precursor to 16 and 973 mg of the precursor to 17 (determined by NOE and NOESY experiments).
Top Spot: ESI-MS calc for C20H21NO: 291; Found 292 (M+H).
Bottom Spot: ESI-MS calc for C20H21NO: 291; Found 292 (M+H).

Step E

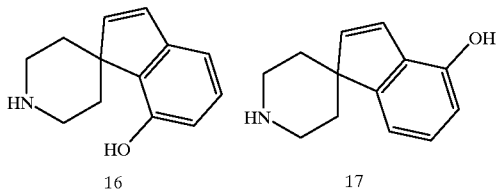

Since the methodology is the same for both 16 and 17, only that used for 16 will be presented in detail:

The intermediate from the above reaction (1.02 g, 3.51 mmol) was combined with triethylamine (0.730 mL, 533 mg, 5.27 mmol) in CH₂Cl₂ (10 mL) at 0° C. and treated dropwise with trifluoroacetic anhidride (737 mg, 3.51 mmol). The reaction mixture was warmed to rt, and a catalytic amount of DMAP was added. After 1 h an additional 0.5 equiv. of trifluoroacetic anhidride was added and the reaction mixture was permitted to stir for 72 h. The reaction mixture was then diluted with CH₂Cl₂, washed with 1N HCl, saturated NaHCO₃ solution and brine, dried over MgSO₄, filtered and concentrated to afford 1.12 g of crude trifluoroacetamide product. This product was dissolved in CH₂Cl₂ and treated with 1.0 M BBr₃ in CH₂Cl₂ (2.9 mL, 2.9 mmol). The reaction mixture was stirred at rt under N₂ for 1.25 h then poured into saturated NaHCO₃ solution which, in turn, was washed with CH₂Cl₂. The organic layer was washed with brine, dried over MgSO₄, filtered and concentrated. Purification by MPLC (40% EtOAc/hexanes) afforded 576 mg of debenzylated intermediate. A portion of this intermediate (537 mg, 1.81 mmol) was dissolved in MeOH (~5 mL) and treated with NaOH (144 mg, 3.61 mmol) in ~3 mL of water. The reaction mixture was stirred for one h and concentrated to afford crude product which was used as is.
ESI-MS calc for C13H15NO: 201; Found 202 (M+H).

INTERMEDIATES 18 AND 19

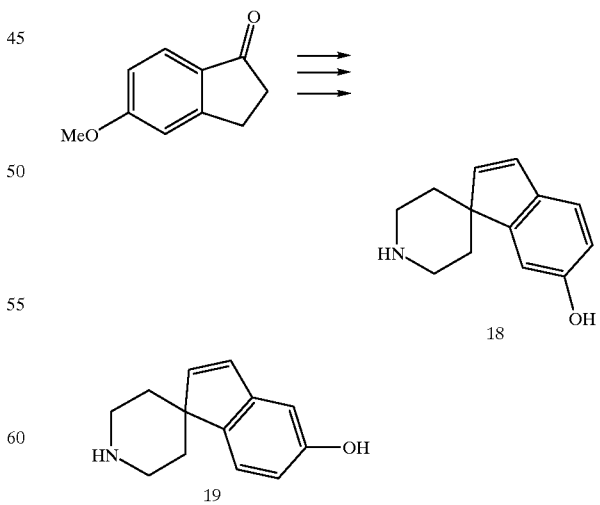

Intermediates 18 and 19 were prepared in the same way as 16 and 17 except the commercially available starting material was 3-methoxy indanone.

INTERMEDIATES 20 AND 21

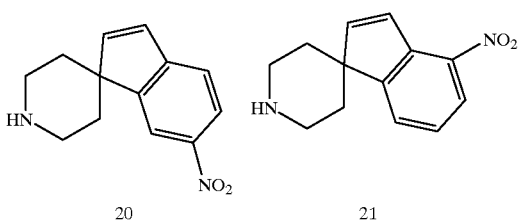

Step A

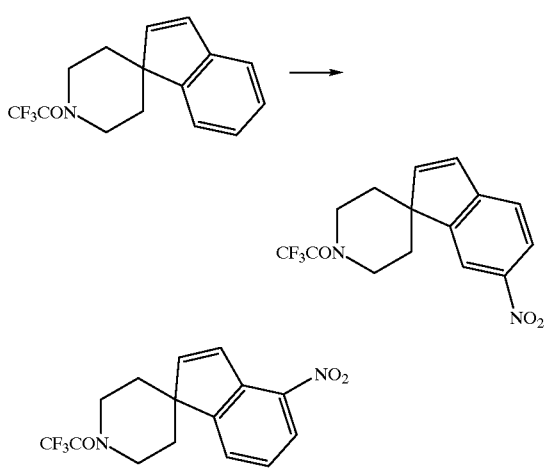

To a cooled solution (0° C.) of spiroindenepiperidine trifluoroacetamide (2.32 g, 8.23 mmol) in acetic anhydride (30 mL) was added fuming $HNO_3$ (90%, 864 mg, 12.4 mmol) dropwise. The reaction mixture was allowed to warm to rt and stir overnight. The reaction mixture was poured onto ice and extracted with ether (3×). The combined ethereal layers were washed with brine (2×), dried over $MgSO_4$, filtered and concentrated. The crude product was purified by MPLC, eluting with 30% EtOAc/hexanes, to afford two primary products which were identified by H NMR to be the para (1.59 g) and ortho (271 mg) isomers, respectively.

Step B

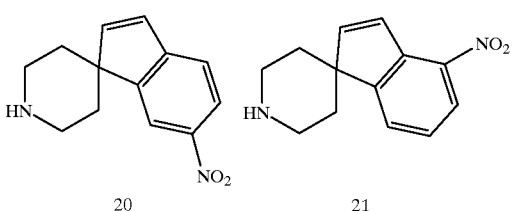

Hydrolysis of the trifluoroacetamide was identical for 20 and 21, therefore only the preparation of 20 will be detailed below.

The para isomer from Step A above (248 mg, 0.759 mmol) was dissolved in methanol (3 mL) and NaOH (46 mg, 1.14 mmol) was added in 0.5 mL water. The reaction mixture was concentrated after one h and the crude product was used "as is".

EXAMPLE 1

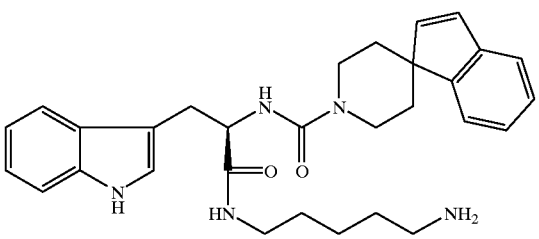

The title compound as a HCl salt was prepared by coupling Intermediate 1 and Intermediate 6 according to the general procedure 1. The resulting amide was purified and then subjected to General procedure 6 to remove the Boc protecting group.

ESI-MS calc. for C30H37N5O2: 499; Found 500(M+H).

Similarly the following additional examples are prepared using commercially available diamines monoprotected with Boc as shown in the preparation of Intermediate 6.

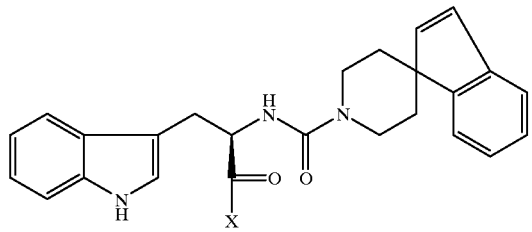

| Entry | X | MF FAB-MS (M + 1) |
|---|---|---|
| 2 | —NH(CH$_2$)$_4$NH$_2$ | 486 |
| 3 | —NH(CH$_2$)$_6$NH$_2$ | 514 |
| 4 | —NH(CH$_2$)$_3$NH$_2$ | 472 |
| 5 |  | 534 |
| 6 | | 540 |
| 7 | 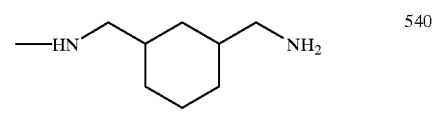 | 512 |
| 8 | 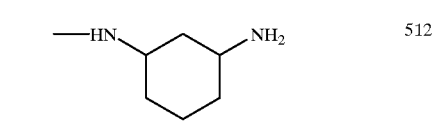 | 512 |

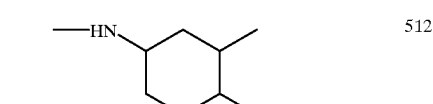

EXAMPLE 9

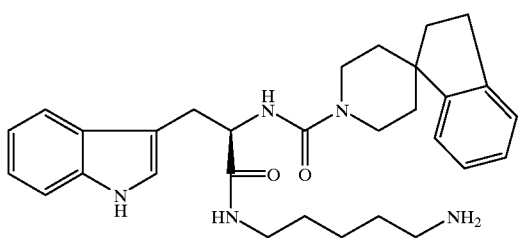

Hydrogenation of the product from Example 1 according to General Procedure 4 yielded the title compound.

ESI-MS calc. for C30H39N5O2: 501; Found 502(M+H).

EXAMPLE 10

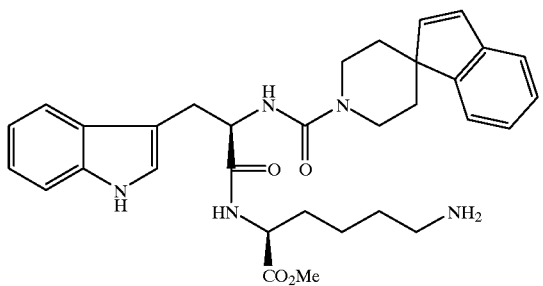

The title compound as a HCl salt was prepared by coupling Intermediate 3 ( mg, mmol) and Intermediate 6 according to the General Procedure 2 for urea formation. The resulting urea was purified and then subjected to General Procedure 6 to remove the Boc protecting group.

ESI-MS calc. for C32H39N5O4: 557; Found 558(M+H).

EXAMPLE 11

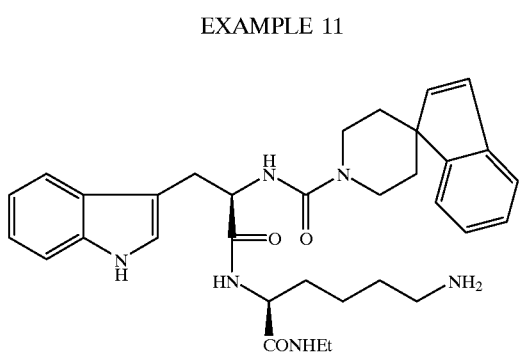

ESI-MS calc. for C33H42N6O3: 570; Found 571 (M+H).

Step A

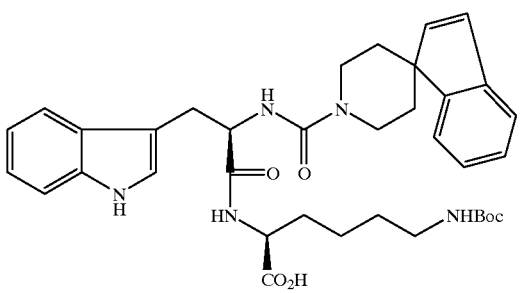

The title compound from Example 9 ( 11.0g, 16.7 mmol) was saponified according the the General procedure 5 to give the acid (9.89 g, 15.4 mmol).

ESI-Mass cacl. for C36H45N5O6: 643; found 644 (M+H)

Step B

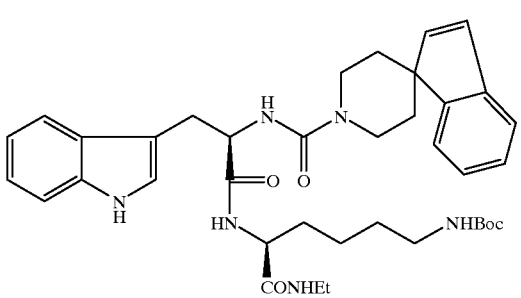

Coupling of the intermediate from the previous step with ethyl amine hydrochloride (250 mg, 0.39 mmol) according to the General Procedure 2 gave the ethyl amide(209 mg, 0.31 mmol).

Step C

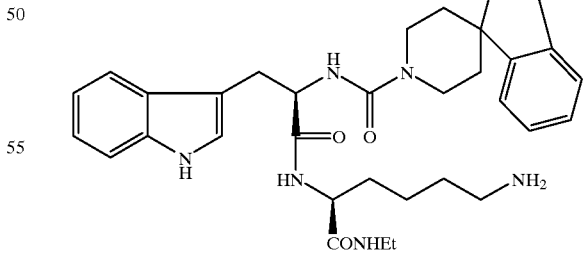

Removal of the Boc protecting group from the intermediate from the previous step (185 mg, 0.276 mmol) according to General procedure 6 gave the title compound (164 mg, 0.27 mmol). ESI-Mass cacl. for C33H42N6O3: 570; found 571.

Similarly, the following compounds are prepared from the corresponding amines:

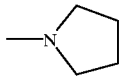

| Entry | X | MF FAB-MS (M + 1) |
|---|---|---|
| 12 | —NH$^i$Pr | 585 |
| 13 | —NH$^t$Bu | 599 |
| 14 | —NH$^i$Bu | 599 |
| 15 | —NMe$_2$ | 571 |
| 16 | ![pyrrolidine] | 597 |

Similarly, the following compounds are prepared from the corresponding amines:

| Entry | X | MF FAB-MS (M + 1) |
|---|---|---|
| 18 | (N-piperidine-spiroindoline-N-SO$_2$Me) | 681 |
| 19 | (N-piperidine-spiroindoline-N-SO$_2$NHMe) | 696 |

EXAMPLE 17

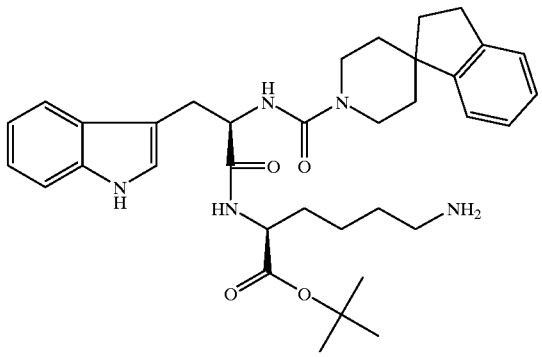

The title compound as a HCl salt was prepared in two steps from Intermediate 4 and spiro(indane-1,4'-piperidine) according to the General procedure 2 for urea formation, followed by removal of the Cbz protecting group according to General procedure 3.

ESI-MS calc. for C35H47N5O4: 601; Found 602(M+H).

EXAMPLE 20

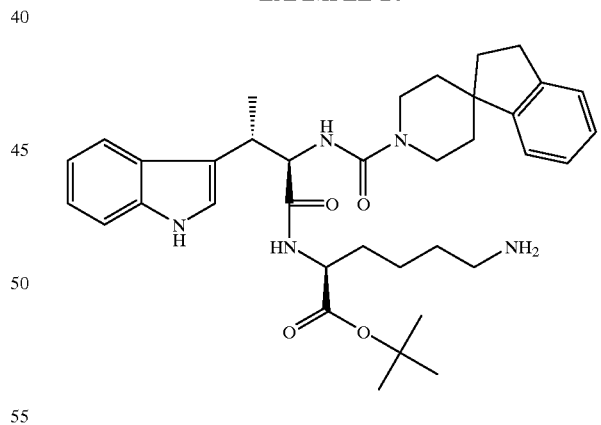

The title compound as a HCl salt was prepared in two steps from Intermediate 5 and spiro(indane-1,4'-piperidine) according to the General procedure 2 for urea formation, followed by removal of the Cbz protecting group according to General procedure 3.

ESI-MS calc. for C36H49N5O4: 615; Found 616(M+H).

Similarly, the following compounds are prepared from the corresponding amines:
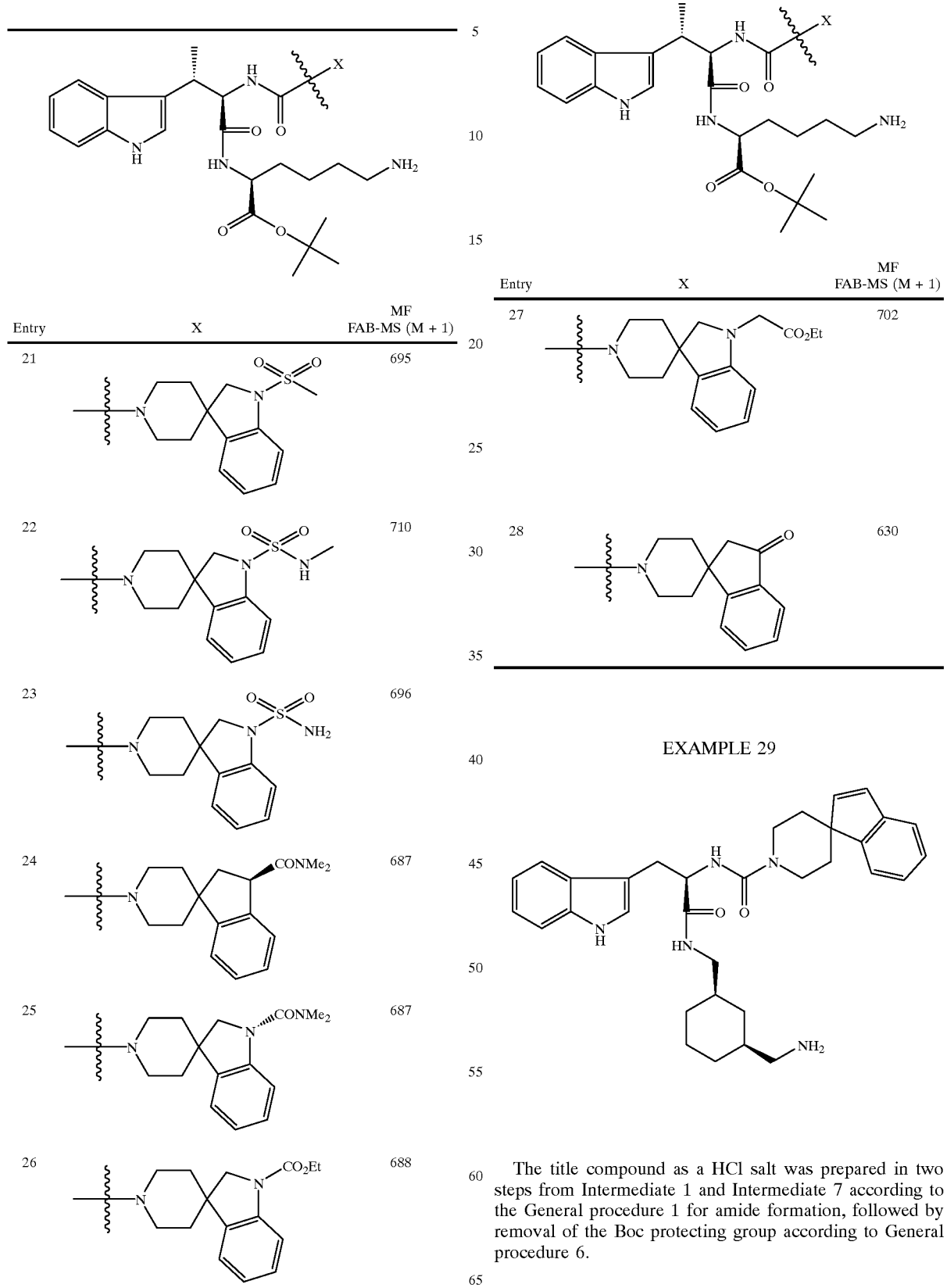
EXAMPLE 29
The title compound as a HCl salt was prepared in two steps from Intermediate 1 and Intermediate 7 according to the General procedure 1 for amide formation, followed by removal of the Boc protecting group according to General procedure 6.
ESI-MS calc. for C33H41N5O2: 539; Found 540 (M+H).

EXAMPLE 29A

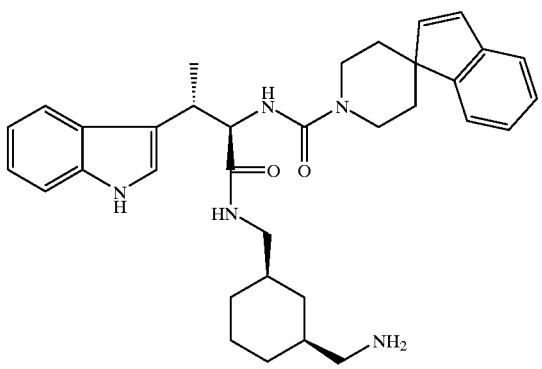

The title compound as a HCl salt was prepared in two steps from Intermediate 2 and Intermediate 7 according to the General procedure 1 for amide formation, followed by removal of the Boc protecting group according to General procedure 6.
ESI-MS calc. for C34H43N5O2: 553; Found 554(M+H).

EXAMPLE 29B

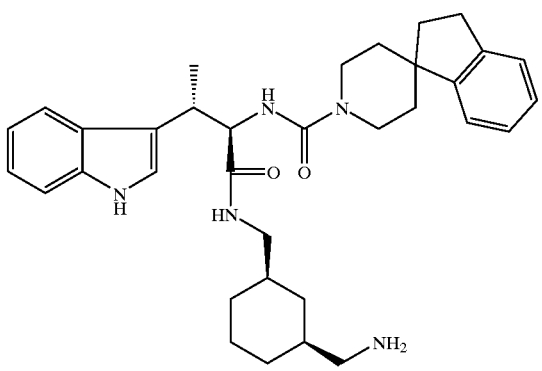

Hydrogenation of the Example 29A according to the procedure of general procedure 4 gave the title compound.
ESI-MS calc. C34H45N5O2: 555; Found 556(M+H).

EXAMPLE 30

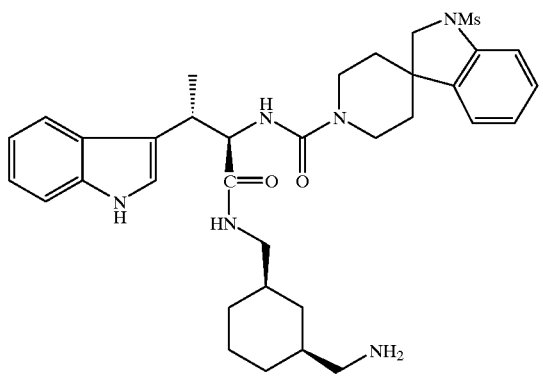

The title compound was prepared from intermediate 7 and (2R,3S)-N-Cbz-β-methyl tryptophan in 4 steps by EDC amide coupling using general procedure 1, deprotection of the Cbz by general procedure 3, urea coupling employing general procedure 2 and final Boc deprotection according to general procedure 6.

ESI-MS calc for C34H46N6O4: 602; Found 603 (M+H).

EXAMPLE 31

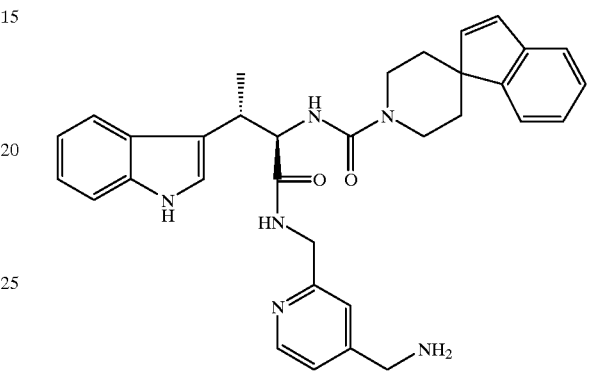

The title compound as di HCl salt was prepared in two steps from Intermediate 2 and Intermediate 8 according to the General procedure 1 for amide formation, followed by removal of the Boc protecting group according to General procedure 6.

ESI-MS calc. for C33H36N6O2: 548; Found 549 (M+H).

EXAMPLE 31A

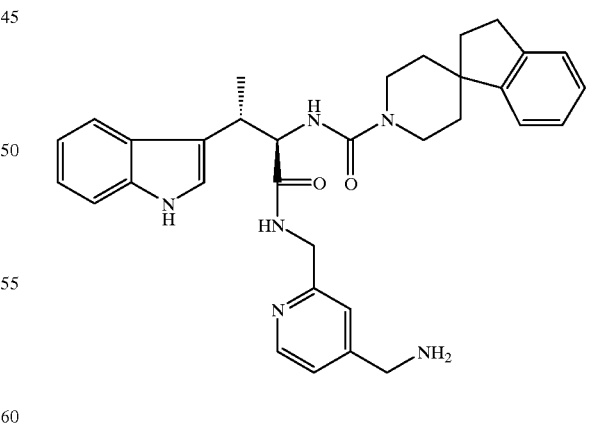

Hydrogenation of Example 9 according to the procedure of general procedure 4 gave the title compound.

ESI-MS calc. for C33H38N6O2: 550; Found 551 (M+H).

EXAMPLE 32

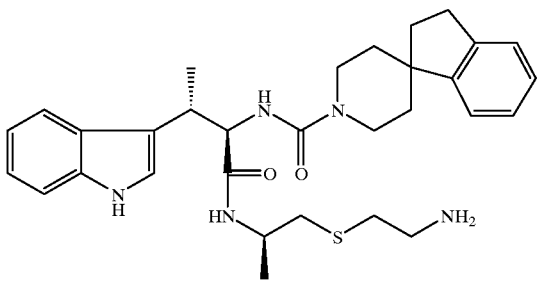

The title compound was prepared in two steps from Intermediate 2A and Intermediate 10 according to the General procedure 1 for amide formation, followed by removal of the trifluoroacetyl protecting group according to General procedure 5.

ESI-MS calc. for $C_{31}H_{41}N_5O_2S$: 547; Found 548(M+H).

EXAMPLE 32A

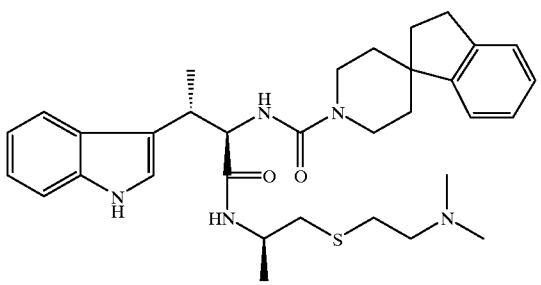

To a stirred solution of compound from Example 32 (120 mg, 0.205 mmol) and formaldehyde (83 µl, mmol) and NaOAc (84mg, 1.025 mmol) in methanol (10 mL) at ambient temperature, was added NaBH3CN (64 mg, 1.025 mmol). The reaction mixture was stirred overnight, and then the mixture was evaporated to dryness . The mixture was redissolved in cold NaHCO3 and extracted with DMC. The organic layer was dried over MgSO4 and evaporated. Prep TLC purification gave the desired product (101 mg).

ESI-MS calc. for $C_{33}H_{45}N_5O_2S$: 595; Found 576(M+H).

EXAMPLE 33

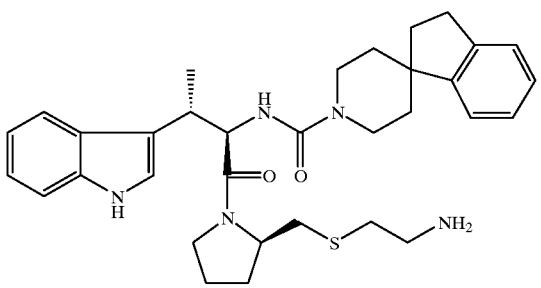

The title compound was prepared in two steps from Intermediate 2A and Intermediate 10A according to the General procedure 1 for amide formation, followed by removal of the trifluoroacetyl protecting group according to General procedure 5.

ESI-MS calc. for $C_{33}H_{43}N_5O_2S$: 573; Found 574 (M+H).

EXAMPLE 34

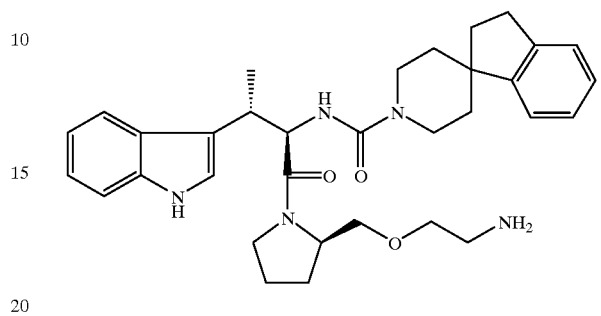

The title compound was prepared in two steps from Intermediate 2A and Intermediate 10 according to the General procedure 1 for amide formation, followed by reduction of the azide according to General procedure 4.

ESI-MS calc. for $C_{33}H_{43}N_5O_3$: 557; Found 558 (M+H).

EXAMPLE 34A

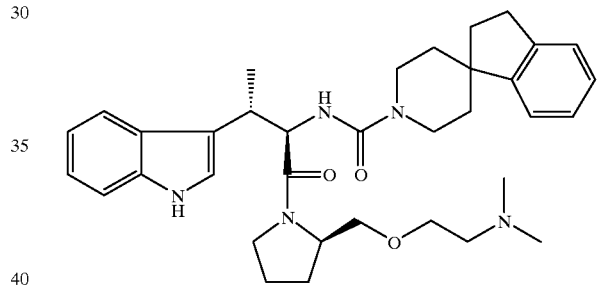

Prepared from Example 34 similarly as described in Example 32A.
ESI-MS calc. for $C_{35}H_{47}N_5O_3$: 585; Found 586(M+H).

EXAMPLE 35

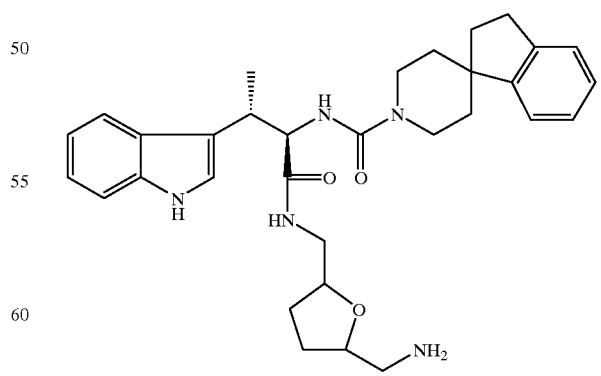

Standard EDC coupling of intermediate 2A with intermediate 12 according to general procedure 1 [72% yield, ESI-MS calc for $C_{37}H_{49}N_5O_5$: 643; Found 644 (M+H)], followed by BOC protecting group removal according to general procedure 6 (88% yield) afforded the title compound as a mixture of isomers.

ESI-MS calc for C32H41N5O3: 543; Found 544 (M+H).

EXAMPLE 36

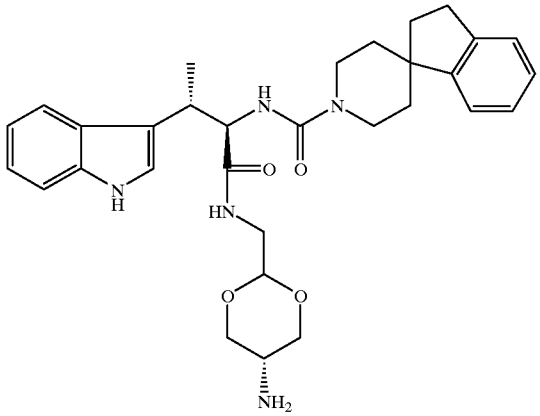

The title compound was prepared from intermediate 14 and (2R,3S)-N-BOC-β-methyl tryptophan in 4 steps by EDC amide coupling using general procedure 1, deprotection of the BOC by general procedure 6, urea coupling employing general procedure 2 and final Cbz deprotection according to general procedure 3.

ESI-MS calc for C30H39N5O4: 533; Found 534 (M+H).

EXAMPLE 37

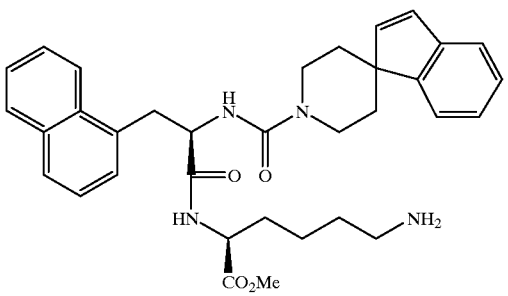

The title compound was prepared in 4 steps from D-1-naphthylalanine methylester by urea coupling according to general procedure 2, saponification of the methyl ester according to general procedure 5 [ESI-MS calc for C27H26N2O3: 426; Found 427 (M+H)], EDC amide condensation with H-Lys(Boc)-OMe by general procedure 1 [ESI-MS calc for C39H48N4O6: 668; Found 669 (M+H)], and BOC deprotection using general procedure 6.

ESI-MS calc for C34H40N4O4: 568; Found 569 (M+H).

Similarly the following additional examples were prepared using commercially available materials.

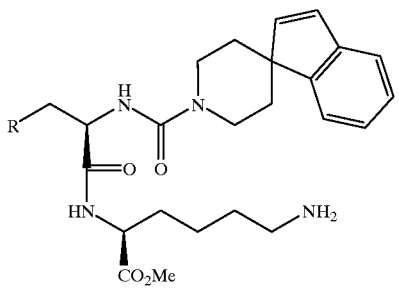

| Entry | R | MF FAB-MS (M + 1) |
|---|---|---|
| 38 | phenyl | 519 |
| 39 | benzyl (with 1,4-butane diamine) | 498 |
| 40 | benzyloxy | 549 |
| 41 | 2-naphthyl | 569 |
| 42 | 3,4-dichlorophenyl | 588 |
| 43 | 3-benzothiazolyl | 575 |
| 44 | 7-aza-indolyl | 559 |
| 45 | 4-chlorophenyl | 554 |
| 46 | 2-chlorophenyl | 554 |
| 47 | 4-biphenyl | 595 |
| 48 | 2-phenylethyl | 547 |
| 49 | 4-hydroxyphenyl | 535 |

Biological Assays

The ability of compounds of the present invention to act as somatostatin agonist can be determined by the following in vitro assays, which is disclosed in Rens-Domiano, et al., Pharmacological Properties of Two Cloned Somatostatin Receptors, *Mol. Pharm.*, 42:28–34 (1992) and incorporated herein.

Receptor Expression Constructs

Mammalian expression vectors containing full length coding sequences for hSSTR1-5 were constructed as follows: Fragments of genomic DNA carrying the various human somatostatin receptors were inserted into the multiple cloning site of pcDNA3 (Invitrogen). The fragments used were a 1.5-kb PstI-XmnI fragment for hSSTR1, 1.7-kb BamHI-HindIII fragment for hSSTR2, 2.0-kb NcoI-HindIII fragment for hSSTR3, a 1.4-kb NheI-NdeI fragment for hSSTR4, and a 3.2-kb XhoI-EcoRI fragment for hSSTR5.

Transfection

CHO-K1 cells were obtained from American Type Culture Collection (ATCC) and grown in alpha-MEM containing 10% fetal calf serum. Cells were stably transfected with DNA for all 5 hSSTRs using lipofectamine. Neomycin resistant clones were selected and maintained in medium containing G418 (400 μg ml).

Receptor Binding Assay

Cells were harvested 72 hr after transfection to 50 mM Tris-HCl, pH 7.8, containing 1 mM EGTA, 5 mM $MgCl_2$, 10 μg/ml leupeptin, 10 μg/ml pepstatin, 200 μg/ml bacitracin, and 0.5 μg/ml aprotinin (buffer 1) and were centrifuged at 24,000×g for 7 min at 4°. The pellet was homogenized in buffer 1 using a Brinkman Polytron (setting 2.5, 30 sec). The homogenate was then centrifuged at 48,000 μg for 20 min at 4° C. The pellet was homogenized in buffer 1 and the membranes were used in the radioligand binding assay. Cell membranes (approximately 10 μg of protein) were incubated with $^{125}$I-Tyr$^{11}$-somatostatin (0.2 nM; specific activity, 2000 Ci/mmol; NEN) in the presence or absence of competing peptides, in a final volume of 200 μl, for 30 min at 25°. Nonspecific binding was defined as the radioactivity remaining bound in the presence of 100 nM somatastatin. The binding reaction was terminated by the addition of ice-cold 50 nM Tris-HCl buffer, pH 7.8, and rapid filtration with 12 ml of ice-cold Tris HCl buffer, and the bound radioactivity was counted in a gamma scintillation spectrophotometer (80% efficiency). Data from radioligand binding studies were used to generate inhibition curves. IC$_{50}$ values were obtained from curve-fitting performed with the mathematical modeling program FITCOMP, available through the National Institutes of Health-sponsored PROPHET System.

Inhibition of Forskolin-Stimulated cAMP Accumulation

Cells used for cAMP accumulation studies were subcultured in 12-well culture plates. COS-7 cells were transfected 72 hr before the experiments. Culture medium was removed from the wells and replaced with 500 μl of fresh medium containing 0.5 mM isobutylmethylxanthine. Cells were incubated for 20 min at 37°. Medium was then removed and replaced with fresh medium containing 0.5 mM isobutylmethylxanthine, with or without 10 μM forskolin and various concentrations of test compound. Cells were incubated for 30 min at 37°. Medium was then removed, and cells were sonicated in the wells in 500 μL of 1 N HCl and frozen for subsequent determination of cAMP content by radioimmunassay. Samples were thawed and diluted in cAMP radioimmunassay buffer before analysis of cAMP content using the commercially available assay kit from NEW/DuPont (Wilmington, Del.).

Inhibition of Growth Hormone Release

Functional activity of the various compounds was evaluated by quantitating release of growth hormone secretion from primary cultures of rat anterior pituitary cells. Cells were isolated from rat pituitaries by enzymatic digestion with 0.2% collagenase and 0.2% hyaluronidase in Hank's balanced salt solution. The cells were suspended in culture medium and adjusted to a concentration of 1.5×10$^5$ cells per milliliter, and 1.0 ml of this suspension was placed in each well of a 24-well tray. Cells were maintained in a humidified 5% CO$_2$-95% air atmosphere at 37° C. for 3 to 4 days. The culture medium consisted of Dulbecco's modified Eagle's medium containing 0.37% NaHCO$_3$, 10% horse serum, 2.5% fetal bovine serum, 1% nonessential amino acids, 1% glutamine, 1% nystatin, and 0.1% gentamycin. Before testing compounds for their capacity to inhibit GH release, cells were washed twice 1.5 hours before and once more immediately before the start of the experiment with the above culture medium containing 25 mM Hepes (pH 7.4). The compounds of the insant invention were tested in quadruplicate by adding them in 1 ml of fresh medium to each well and incubating them at 37° C. for 15 min. After incubation, the medium was removed and centrifuged at 2000 g for 15 min to remove any cellular material. The supernatant fluid was removed and assayed for GH by radioimmunoassay.

The compounds of this invention were found to inhibit the binding of somatostatin to its receptor at an IC$_{50}$ of about 30 pM to about 3 μM.

What is claimed is:
1. A compound represented by structural formula I:

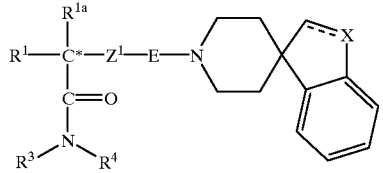

Formula I wherein:
R$^1$ is selected from the group consisting of: C$_1$-C$_6$ alkyl, aryl, aryl (C$_1$-C$_6$ alkyl), heteroaryl, heteroaryl (C$_1$-C$_6$ alkyl), (C$_3$-C$_7$ cycloalkyl)(C$_1$-C$_6$ alkyl)—, (C$_1$-C$_5$ alkyl)—K—(C$_1$-C$_5$ alkyl )—, aryl(C$_0$-C$_5$ alkyl)—K—(C$_1$-C$_5$ alkyl)—, and (C$_3$-C$_7$ cycloalkyl)(C$_0$-C$_5$ alkyl)—K—(C$_1$-C$_5$ alkyl)—, where K is —O—, —S(O)—, —N(R$^2$)C(O)—, —C(O)N(R$^2$)—, —CR$^2$=CR$^2$—, or —C≡C—, where R$^2$ and alkyl may be further substituted by 1 to 5 halogen, S(O)$_m$R$^{2a}$, 1 to 3 of OR$^{2a}$ or C(O)OR$^{2a}$, and aryl and heteroaryl are defined within, and where the aryl and heteroaryl are unsubstituted or substituted with a substitutent selected from: 1 to 3 of C$_1$-C$_6$ alkyl, 1 to 3 of halogen, 1 to 2 of —OR$^2$, methylenedioxy, —S(O)$_m$R$^2$, 1 to 2 of —CF$_3$, —OCF$_3$, nitro, —N(R$^2$)C(O)(R$^2$), —C(O)OR$^2$, —C(O)N(R$^2$)(R$^2$), —1H-tetrazol-5-yl, —SO$_2$N(R$^2$) (R$^2$), —N(R$^2$)SO$_2$ phenyl, or —N(R$^2$)SO2R$^2$;
R$^2$ & R$^5$ are selected from hydrogen, C$_1$-C$_8$ alkyl, (CH$_2$)$_t$ aryl, and C$_3$-C$_7$ cycloalkyl, and where two C$_1$-C$_6$ alkyl groups are present on one atom, they optionally are joined to form a C$_3$-C$_8$ cyclic ring, optionally including oxygen, sulfur or NR$^{3a}$, where R$^{3a}$ is hydrogen, or C$_1$-C$_6$ alkyl, optionally substituted by hydroxyl; aryl is defined within
R$^{1a}$ is selected from the group consisting of hydrogen, and C$_1$-C$_3$ alkyl;
R$^{2a}$ is selected from the group consisting of hydrogen and C$_1$-C$_3$ alkyl, said alkyl optionally substituted by hydroxyl;
E is selected from the group consisting of —SO$_2$—, —CO (C(R$^2$)2)$_n$—, —C(=N—CN)—, —C(=N—NO$_2$)— and —C(=N—SO$_2$N(R$^2$)2)—;
Z$^1$ is —NR$^{2a}$;
R$^3$ is selected from the group consisting of H, C$_{1-8}$ alkyl, (CH$_2$)$_t$aryl and (CH$_2$)$_t$heteroaryl;
R$^4$ is CH(CO$_2$R$^2$)(CH$_2$)$_n$N(R$^2$)$_2$, CH(R$^2$)—(CH$_2$)$_n$N(R$^2$)$_2$, CH(CO$_2$R$^2$), CHCON(R$^2$)$_2$, CH(CO$_2$R$^2$)CH$_2$W(CH$_2$)$_n$N (R$^2$)$_2$,

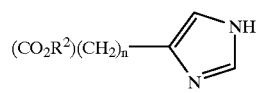

or R$^6$
R$^6$ is:

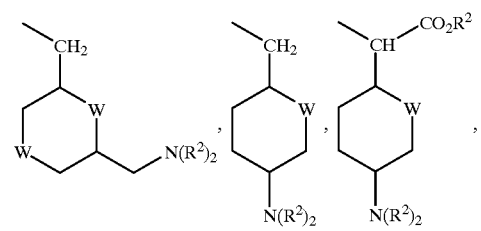

-continued

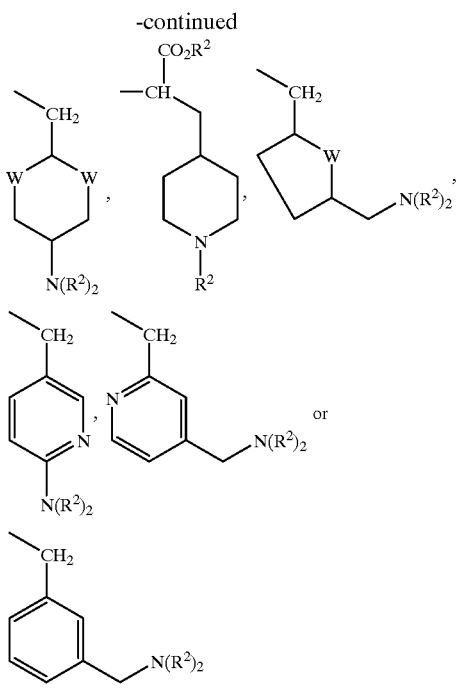

wherein $R^6$ is optionally substituted with 1 to 3 groups of $R^2$, 1 to 3 of halogen, 1 to 2 of —$OR^2$, methylenedioxy, —$S(O)_mR^2$, 1 to 2 of —$CF_3$, —$OCF_3$, —$N(R^2)C(O)(R^2)$, —$C(O)OR^2$, —$C(O)N(R^2)(R^2)$, —$SO_2N(R^2)(R^2)$, —$N(R^2)SO_2$ phenyl, or —$N(R^2)S_2R^2$;

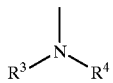

represents one of the following:

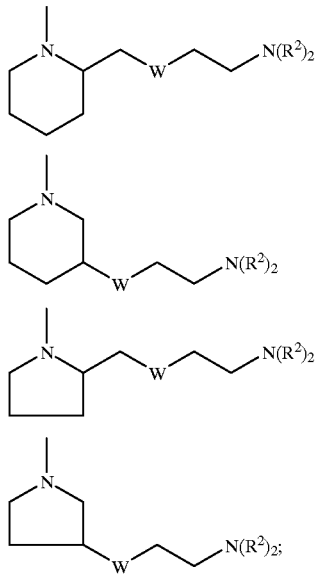

when the dotted line does not represent a bond, X is selected from the group consisting of $CH_2$, $CHCO_2R_2$, $C(O)$, $CHCH_2CO2R^2$, $CHCON(R^2)_2$ and $NSO_2R^2$, and when the dotted line represents a bond, X represents C substituted with $R^5$;

W is selected from the group consisting of O, S, $CH_2$, $N(R^2)C(O)$ and $C(O)N(R^2)$;

m is an integer from 0 to 2;

n is an integer from 0–5;

t is an integer from 0 to 3.

2. A compound of structural formula Ia or Ib:

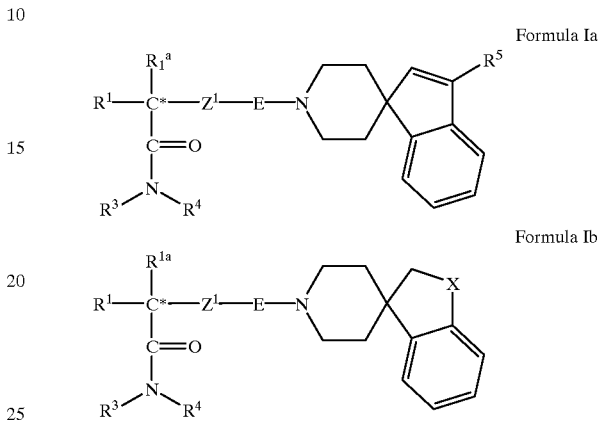

Formula Ia

Formula Ib wherein:

$R^1$ is selected from the group consisting of: $C_1$–$C_6$ alkyl, aryl, aryl ($C_1$–$C_6$ alkyl), heteroaryl, heteroaryl ($C_1$–$C_6$ alkyl), ($C_3$–$C_7$ cycloalkyl)($C_1$–$C_6$ alkyl)—, ($C_1$–$C_5$ alkyl)—K—($C_1$–$C_5$ alkyl )—, aryl($C_0$–$C_5$ alkyl)—K—($C_1$–$C_5$ alkyl)—, and ($C_3$–$C_7$ cycloalkyl)($C_0$–$C_5$ alkyl)—K—($C_1$–$C_5$ alkyl)—, where K is —O—, —S(O)—, —$N(R^2)C(O)$—, —$C(O)N(R^2)$—, —$CR^2$=$CR^2$—, or —C≡C—, where $R^2$ and alkyl may be further substituted by 1 to 5 halogen, $S(O)_mR^{2a}$, 1 to 3 of $OR^{2a}$ or $C(O)OR^{2a}$, and aryl and heteroaryl are defined within, and where the aryl and heteroaryl are unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, —1H-tetrazol-5-yl, —$SO_2N(R^2)(R^2)$, —$N(R^2)SO_2$ phenyl, or —$N(R^2)SO2R^2$;

$R^2$ & $R^5$ are selected from hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl; aryl is defined within $R^{1a}$ is selected from the group consisting of hydrogen, and $C_1$–$C_3$ alkyl;

$R^{2a}$ is selected from the group consisting of hydrogen and $C_1$–$C_3$ alkyl, said alkyl optionally substituted by hydroxyl;

E is selected from the group consisting of —$SO_2$—, —$CO(C(R^2)2)_n$—, —C(=N—CN)—, —C(=N—$NO_2$)— and —C(=N—$SO_2N(R^2)2$)—;

$Z^1$ is —$NR^{2a}$;

$R^3$ is selected from the group consisting of H, $C_{1-8}$ alkyl, $(CH_2)_t$aryl and $(CH_2)_t$heteroaryl;

$R^4$ is $CH(CO_2R^2)(CH_2)_nN(R^2)_2$, $CH(R^2)$—$(CH_2)_nN(R^2)_2$, $CH(CO_2R^2)$, $CHCON(R^2)_2$, $CH(CO_2R^2)CH_2W(CH_2)_nN(R^2)_2$,

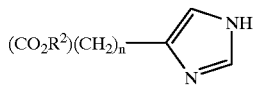

or R⁶

R⁶ is:

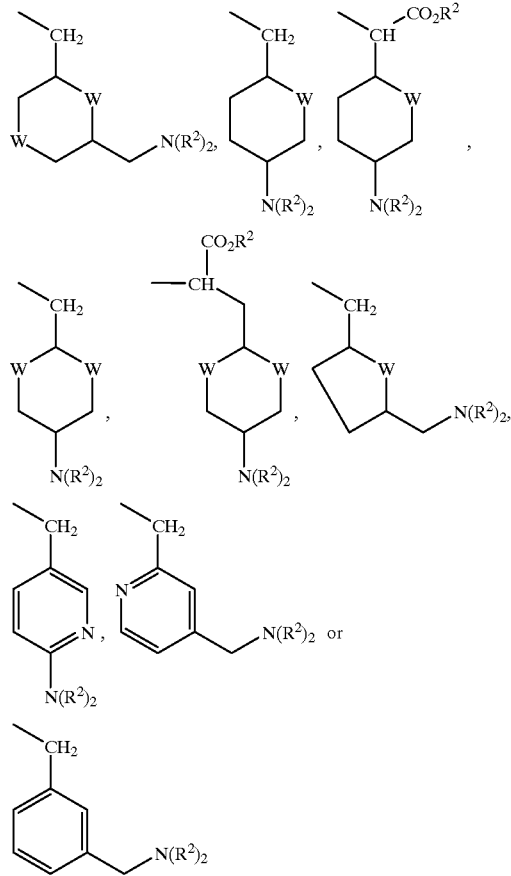

wherein R⁶ is optionally substituted with 1 to 3 groups of $R^2$, 1 to 3 of halogen, 1 to 2 of —$OR^2$, methylenedioxy, —$S(O)_m R^2$, 1 to 2 of —$CF_3$, —$OCF_3$, —$N(R^2)C(O)(R^2)$, —$C(O)OR^2$, —$C(O)N(R^2)(R^2)$, —$SO_2N(R^2)(R^2)$, —$N(R^2)SO_2$ phenyl, or —$N(R^2)S_2R^2$;

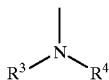

can be

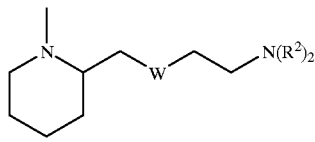

-continued

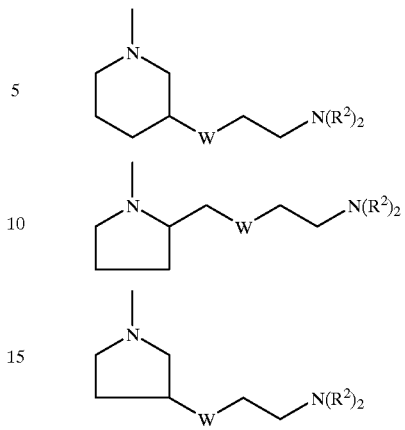

X is selected from the group consisting of $CH_2$, $CHCO_2R_2$, $C(O)$, $CHCH_2CO_2R^2$, $CHCON(R^2)_2$ and $NSO_2R^2$;

W is selected from the group consisting of O, S, $CH_2$, $N(R^2)C(O)$ and $C(O)N(R^2)$;

m is an integer from 0 to 2;

n is an integer from 0–5, and t is an integer from 0 to 3.

3. A compound according to claim 2 having a structural formula Ib-1 or Ib-2:

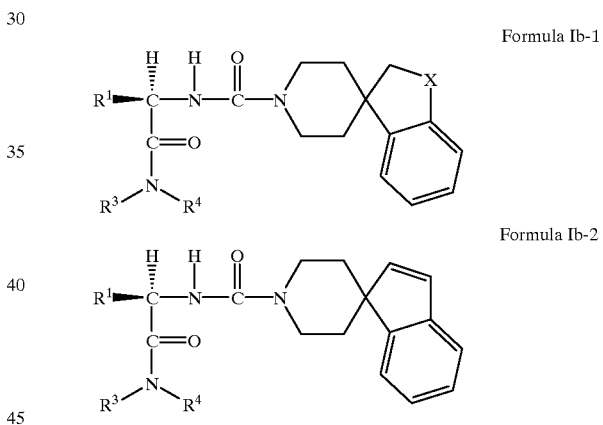

Formula Ib-1

Formula Ib-2 wherein:

$R^1$ is selected from the group consisting of: aryl ($C_1$–$C_6$ alkyl), heteroaryl($C_1$–$C_6$ alkyl), where aryl and heteroaryl is selected from: phenyl, indanyl, benzyloxy, benzothiazolyl, biphenyl, aza-indolyl, benzyl(with 1,4-butane diamine) naphthyl, quinolinyl, indolyl, pyridyl, benzothienyl, benzofuranyl, thiazolyl, and benzimidazolyl, and where the aryl and heteroaryl are unsubstituted or substituted with a substitutent selected from: 1 to 3 of $C_1$–$C_6$ alkyl, 1 to 3 of halogen, 1 to 2 of—$OR^2$, 1 to 2 of —$CF_3$, —$OCF_3$, nitro, $C(O)OR^2$, or —$C(O)N(R^2)(R^2)$;

$R^2$ is selected from: hydrogen, $C_1$–$C_8$ alkyl, and $(CH_2)_t$ aryl, where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl;

$R^3$ is selected from the group consisting of hydrogen, $C_1$–$C_8$ alkyl and $(CH_2)_t$ aryl;

$R^4$ is $CH(CO_2R^2)(CH_2)_nN(R^2)_2$, $CH(R^2)$—$(CH_2)_nN(R^2)_2$, $CH(CO_2R^2)$, $CHCON(R^2)_2$, $CH(CO_2R^2)CH_2W(CH_2)_nN(R^2)_2$,

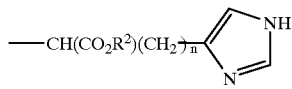

or $R^6$ $R^6$ is

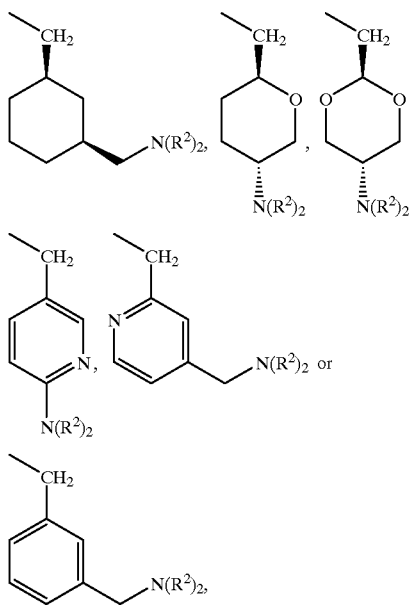

wherein $R^6$ is optionally substituted with 1 to 3 groups of $R^2$, 1 to 3 of halogen, 1 to 2 of —$OR^2$, methylenedioxy, —$S(O)_mR^2$, 1 to 2 of —$CF_3$, —$OCF_3$, —$N(R^2)C(O)(R^2)$, —$C(O)OR^2$, —$C(O)N(R^2)(R^2)$, —$SO_2N(R^2)(R^2)$, —$N(R^2)SO_2$ phenyl, or —$N(R^2)S_2R^2$;

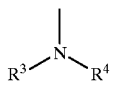

can be

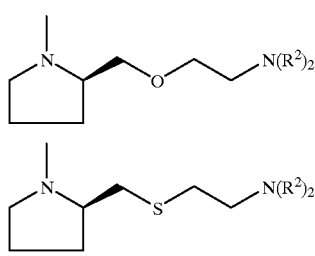

X is selected from the group consisting of $CH_2$, and $NSO_2R^2$;
and all other variables are described above.

4. A compound according to claim 2 wherein:
$R^1$ is

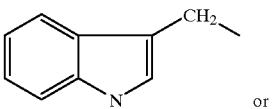

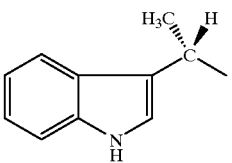

which may be substituted by 1 to 3 of $R^2$, 1 to 3 of halogen, 1 to 2 of —$OR^2$, 1 to 2 of —$CF_3$, —$OCF_3$, nitro, —$C(O)OR^2$, —$C(O)N(R^2)(R^2)$;

$R^3$ is selected from hydrogen or methyl;
$R^4$ is $CH(CO_2But)(CH_2)_4NH_2$, $CH(R^2)$—$(CH_2)_4NH_2$, $CH(CO_2But)CH_2WCH_2CH_2NH_2$, or $R^6$
wherein $R^6$ is

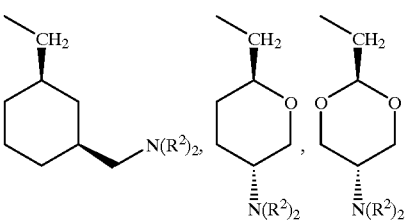

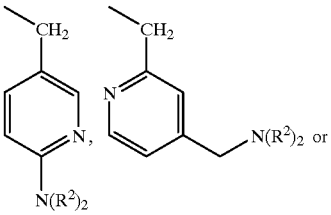

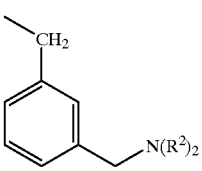

which is optionally substituted with 1 to 3 groups of $R^2$, 1 to 3 of halogen, 1 to 2 of—$OR^2$, 1 to 2 of—$CF_3$);
X is selected from the group consisting of $CH_2$, and $NSO_2CH_3$;
and all other variables are described above.

5. A compound according to claim 2 which is:

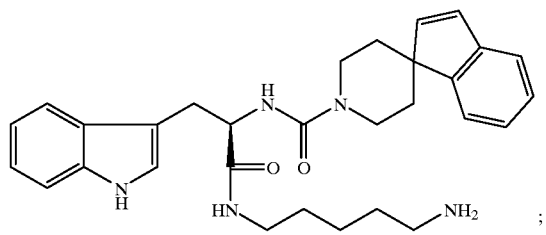

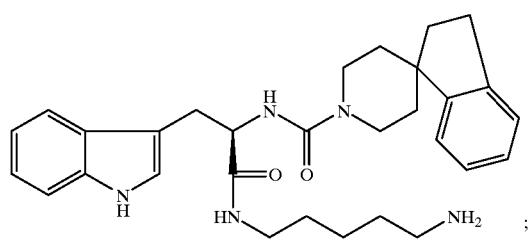
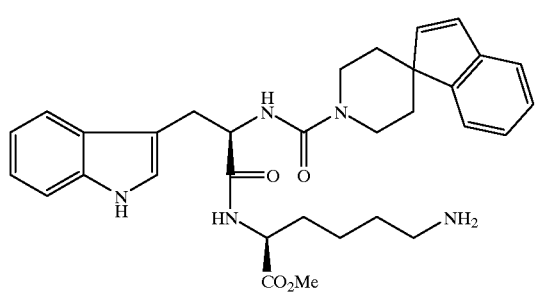
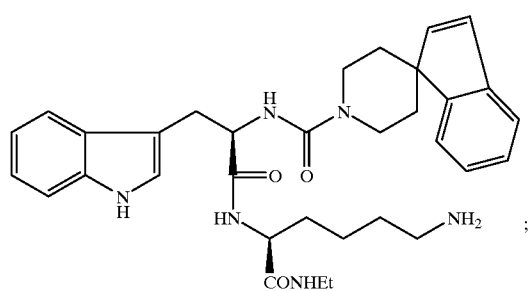
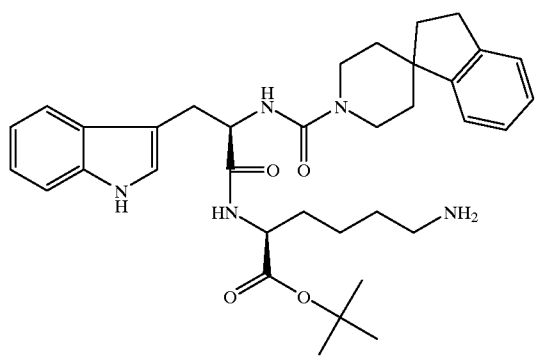
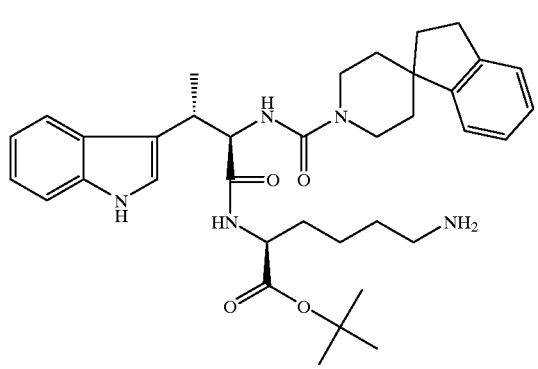
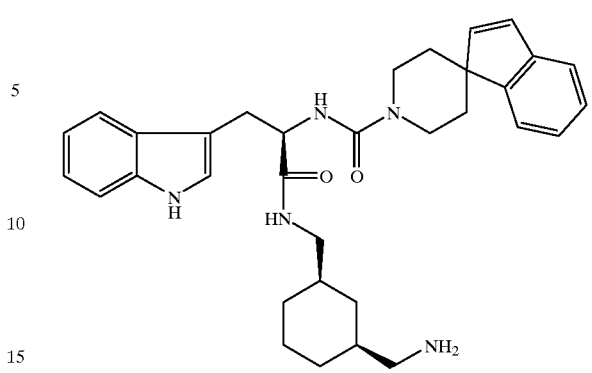
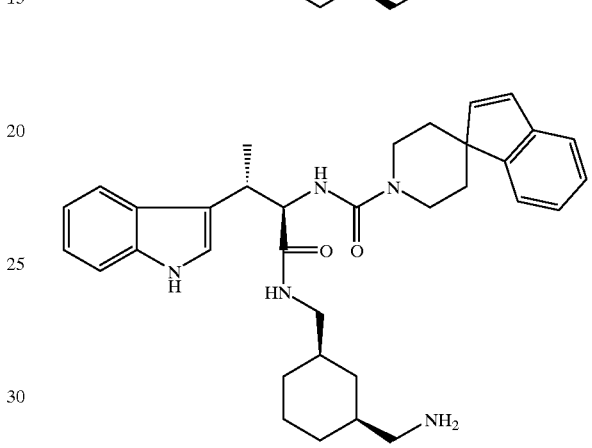
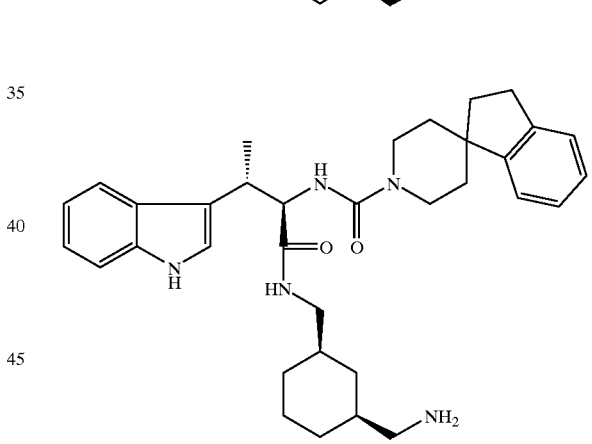
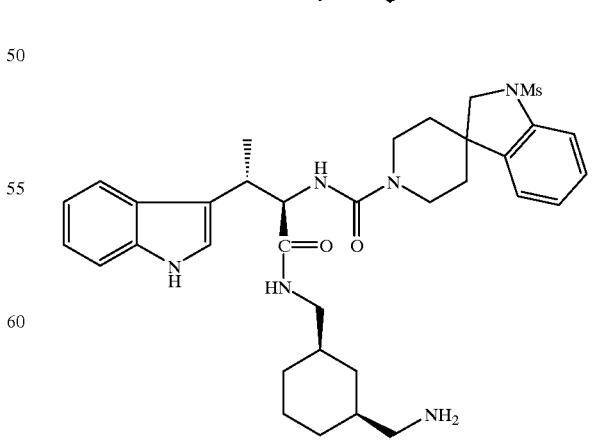

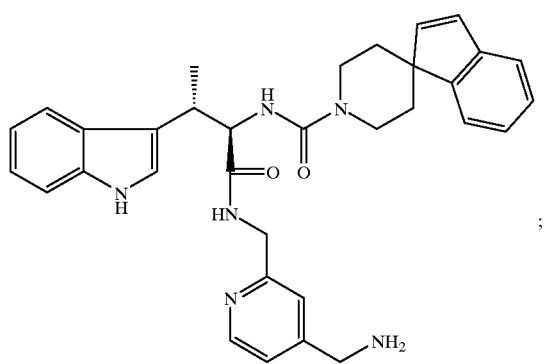
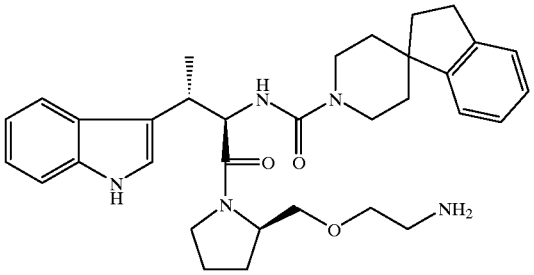
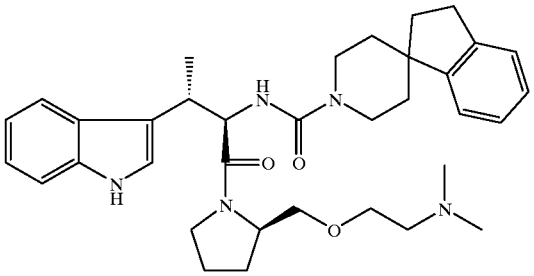
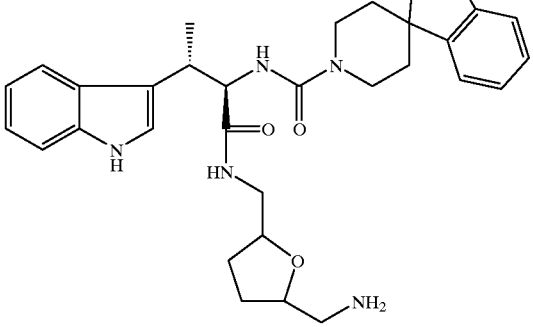
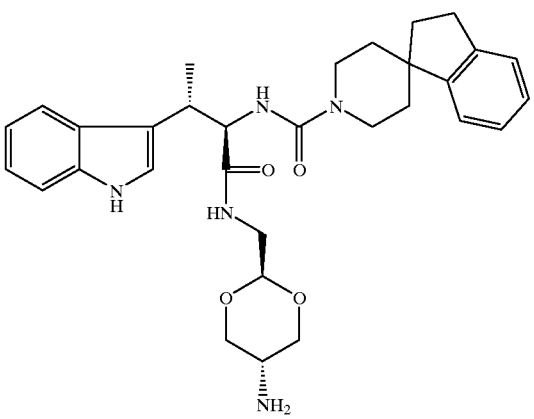
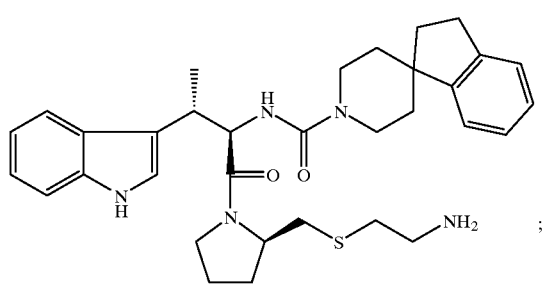
and
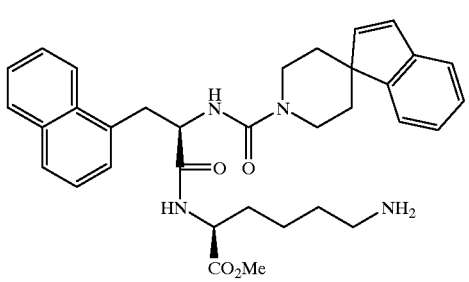

6. A compound according to claim 2 which is depicted in the tables below:
TABLE
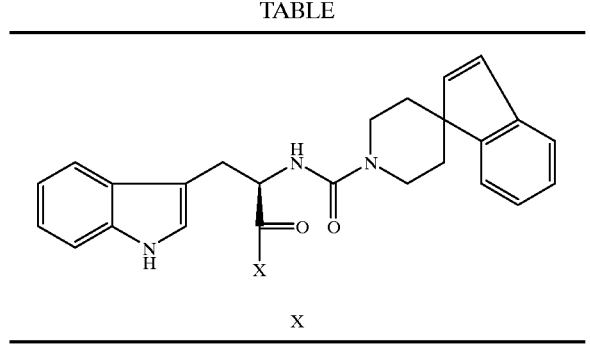
X
—NH(CH₂)₄NH₂,
—NH(CH₂)₆NH₂,
—NH(CH₂)₃NH₂,
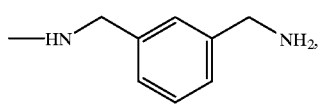
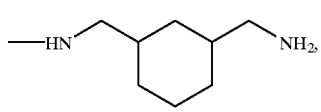
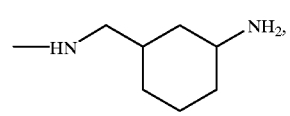
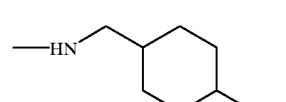
TABLE
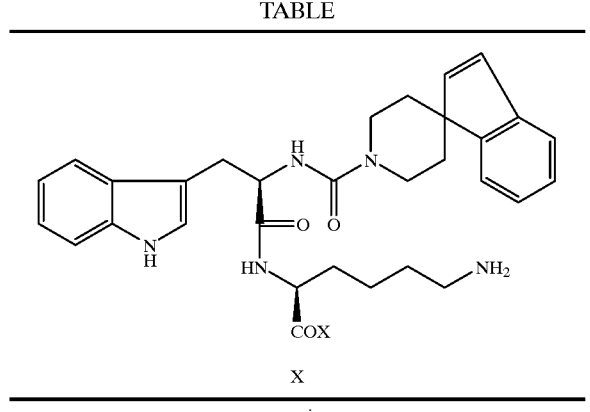
X
—NHⁱPr,
—NHᵗBu,
—NHⁱBu,
—NMe₂,
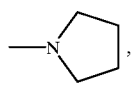
TABLE
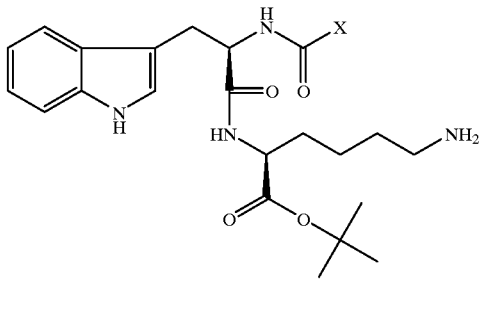
X
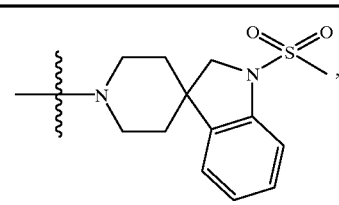
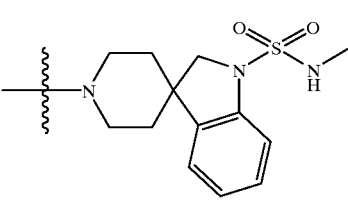
TABLE
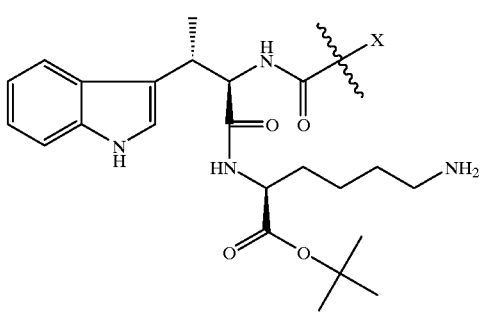
X
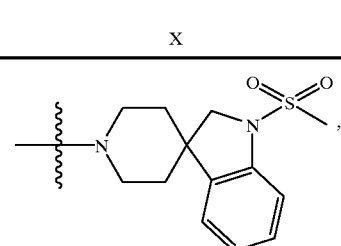
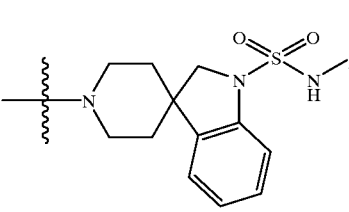

TABLE-continued

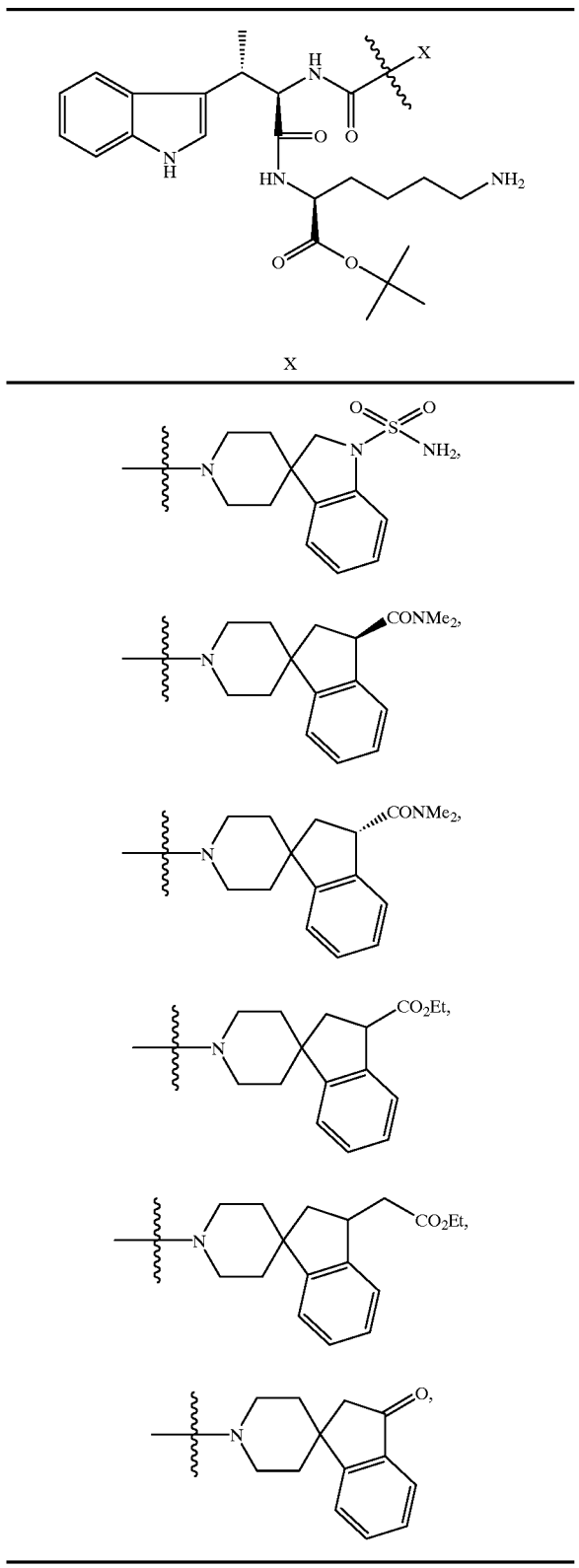

TABLE

R
phenyl,
benzyl (with 1,4-butane diamine),
benzyloxy,
2-naphthyl,
3,4-dichlorophenyl,
3-benzothiazolyl,
7-aza-indolyl,
4-chlorophenyl,
2-chlorophenyl,
4-biphenyl,
2-phenylethyl and
4-hydroxyphenyl.

7. A method of treating diabetes in a mammal in need of such treatment, which comprises administering to said mammal an effective amount of a somatostatin agonist.

8. A method of treating diabetes in a mammal in need of such treatment, which comprises administering to said mammal an effective amount of a somatostatin agonist of claim 1.

9. A method of treating acromegaly in a mammal in need of such treatment, which comprises administering to said mammal an effective amount of a somatostatin agonist of claim 1.

10. A method of treating restenosis in a mammal in need of such treatment, which comprises administering to said mammal an effective amount of a somatostatin agonist of claim 1.

11. A method of treating retinopathy in a mammal in need of such treatment, which comprises administering to said mammal an effective amount of a somatostatin agonist of claim 1.

12. A method of treating depression in a mammal in need of such treatment, which comprises administering to said mammal an effective amount of a somatostatin agonist.

13. A method of treating depression in a mammal in need of such treatment, which comprises administering to said mammal an effective amount of a somatostatin agonist of claim 1.

14. A pharmaceutical composition comprising a therapeutically effective amount of a compound according to claim 1 and a pharmaceutically acceptable carrier.

* * * * *